United States Patent [19]

Wakatsuka et al.

[11] Patent Number: 4,562,204

[45] Date of Patent: Dec. 31, 1985

[54] TRANS-Δ²-PROSTAGLANDIN D DERIVATIVES, PROCESS FOR THEIR PREPARATION AND COMPOSITIONS CONTAINING THEM

[75] Inventors: Hirohisa Wakatsuka; Takashi Yamato, both of Takatsuki; Shinsuke Hashimoto, Ibaraki, all of Japan

[73] Assignee: Ono Pharmaceutical Co., Ltd., Osaka, Japan

[21] Appl. No.: 508,560

[22] Filed: Jun. 28, 1983

[30] Foreign Application Priority Data

Jun. 30, 1982 [JP] Japan .................. 57-112756

[51] Int. Cl.[4] .................. C07C 177/00; A61K 31/557
[52] U.S. Cl. .................. 514/530; 514/570; 514/573; 514/908; 560/51; 560/53; 560/118; 560/121; 562/459; 562/463; 562/500; 562/503; 536/103
[58] Field of Search .................. 560/121, 51, 53, 118; 562/503, 459, 463, 500; 514/530, 573, 570; 536/103

[56] References Cited

U.S. PATENT DOCUMENTS 3,954,844 5/1976 Colton .................. 260/488
4,123,463 10/1978 Bundy .................. 260/586

FOREIGN PATENT DOCUMENTS 2212146 7/1974 France .................. 560/121

OTHER PUBLICATIONS

Corey, Experiment 19, 39 1084 (1983).

*Primary Examiner*—Robert Gerstl
*Attorney, Agent, or Firm*—Stevens, Davis, Miller & Mosher

[57] ABSTRACT

Trans-Δ²-prostaglandin D derivatives of the formula:

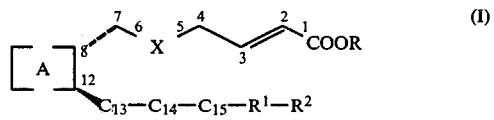

wherein
[A] is a group of the formula:

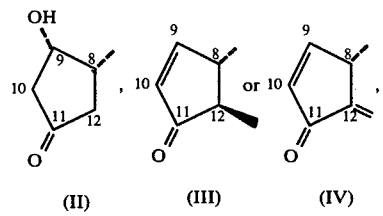

X is ethylene or cis-vinylene, $C_{13}$–$C_{14}$–$C_{15}$ is:
(i) a group of the formula:

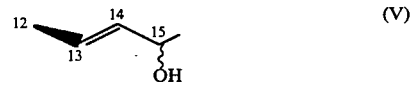

when [A] is a group of the formula (II) or (III), or
(ii) a group of the formula:

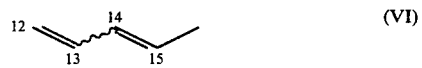

when [A] is a group of the formula (IV), R is hydrogen or alkyl, $R^1$ is a single bond or alkylene, $R^2$ is alkyl, cycloalkyl, phenyl or phenoxy, the double bonds between $C_2$–$C_3$ and between $C_{13}$–$C_{14}$ are both E, the double bond between $C_9$–$C_{10}$ is Z and the double bonds between $C_{12}$–$C_{13}$ and between $C_{14}$–$C_{15}$ are E, Z or a mixture thereof, provided that when $R^1$ is a single bond, $R^2$ does not represent a substituted or unsubstituted phenoxy group, and cyclodextrin clathrates and non-toxic salts thereof, possess anti-tumor activity.

20 Claims, No Drawings

TRANS-Δ²-PROSTAGLANDIN D DERIVATIVES, PROCESS FOR THEIR PREPARATION AND COMPOSITIONS CONTAINING THEM

DESCRIPTION

The present invention relates to novel prostaglandin D derivatives, to processes for their production and pharmaceutical compositions containing them.

Prostaglandins are derivatives of prostanoic acid having the following structure:

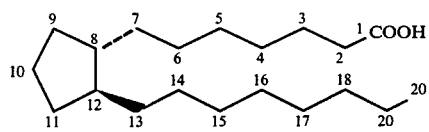

Various types of prostaglandins are known, and their types depend on the structure of the alicyclic ring and the substituents. For example, the alicyclic rings of prostaglandin F (PGF), E (PGE) and D (PGD) have the following structures, respectively:

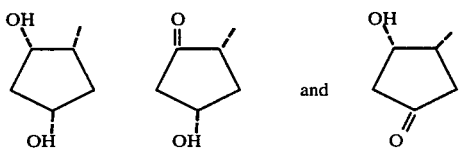

In the above structural formulae or in the other structural formulae in this specification, according to the generally accepted nomenclature, the broken line indicates that the substituent attached thereto is behind the ring plane, i.e. is of the α-configuration, the bold line indicates that the substituent attached thereto is in front of the ring plane, i.e. is of the β-configuration, and the wavy line indicates that the substituent attached thereto is of the α-configuration or the β-configuration or a mixture thereof.

These compounds are sub-classified according to the positions of the double bonds in the side chains attached to the alicyclic ring at the 8-position and the 12-position. The PG-1 compound has a trans double bond (trans-Δ¹³) between $C_{13}$–$C_{14}$ and the PG-2 compound has a cis double bond between $C_5$–$C_6$ and a trans double bond between $C_{13}$–$C_{14}$ (cis-$\Delta^5$, trans-$\Delta^{13}$). For example, prostaglandin $D_1$ ($PGD_1$) and prostaglandin $D_2$ ($PGD_2$) may be expressed by the following structural formulae respectively:

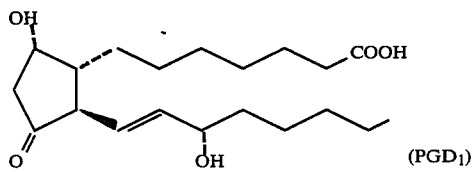

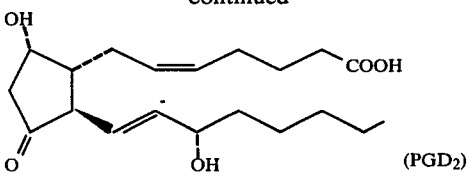

Further, when one or more methylene groups are removed from the aliphatic group attached at the 12-position of the alicyclic ring of a prostaglandin, said compound is known as a nor-prostaglandin according to the general rule of the organic nomenclature, and the number of the removed methylene groups is indicated by adding di-, tri- etc. before the prefix "nor".

The prostaglandins generally have pharmacological properties. For example, they exert various effects, including the stimulation of contraction of smooth muscles, a hypotensive effect, a diuretic effect, a bronchial dilation effect, the inhibition of lypolysis, the inhibition of platelet aggregation and the inhibition of gastric acid secretion. Therefore, they are useful in treatments of hypertension, thrombosis, asthma and gastric and intestinal ulcers, in the induction of labor and abortion in pregnant mammals, in the prevention of arteriosclerosis and also as diuretics. They are liposoluble substances present in extremely small quantities in the tissues which secrete prostaglandins in vivo in animals.

As a result of research and experimentation to discover novel compounds which have the pharmacological effects of the "natural" prostaglandins, or which have one or more of these properties to an enhanced degree, or which have properties which are not found in the "natural" prostaglandins, it has been discovered that novel compounds in which a trans-double bond has been introduced between $C_2$–$C_3$ of $PGD_1$ and $PGD_2$ and analogues thereof (trans-$\Delta^2$-PGD analogues), and related novel compounds in which, in addition, the hydroxy group attached at the 9-position thereof has been removed to introduce a cis-double bond between $C_9$–$C_{10}$ (trans-$\Delta^2$-9-deoxy-$\Delta^9$-PGD analogues), and further related novel compounds in which, in addition, the hydroxy group attached to the 15-position has been removed to introduce double bonds between the $C_{12}$–$C_{13}$ and $C_{14}$–$C_{15}$ positions have a surprisingly strong anti-tumor effect whereas they have no or very weak pharmacological properties possessed by the "natural" prostaglandins.

Heretofore, there have been filed several patent applications relating to PGD analogues. For example, there are disclosed 9-deoxy-$\Delta^9$-$PGD_2$ and alkyl esters thereof in the specification of the U.S. Pat. No. 3,954,844 (Derwent No. 37947X); compounds wherein various substituents have been introduced into the aliphatic group attached to the 12-position are described in the specification of the U.S. Pat. No. 4,016,184 (Derwent No. 24680Y); and further compounds in which the carboxyl group at the 1-position of the PGD compounds has been replaced by various functional groups are described in the specifications of Belgian Pat. Nos. 840871 (Derwent No. 81216X) and 849963 (Derwent No. 46957Y), and the U.S. Pat. Nos. 4,028,419 (Derwent No. 43349Y), 4,055,602 (Derwent No. 48794Y), 4,032,576 (Derwent No. 48793Y) and 4,176,282 (Derwent No. 89348B).

However, none of the above applications discloses the trans-$\Delta^2$-PGD derivatives of the present invention, or other compounds of the invention which have a double bond between $C_9-C_{10}$, or have double bonds between $C_9-C_{10}$, $C_{12}-C_{13}$ and $C_{14}-C_{15}$.

Furthermore, in addition to their structural differences from known PGD compounds, the novel compounds of the present invention have an effect which has not hitherto been found in the known PGD analogues that is, an anti-tumour effect. The above-described U.S. and Belgian Patent specifications describe only the pharmacological properties known with the natural prostaglandins and none of the applications refers to an anti-tumour effect.

Accordingly, the present invention relates to trans-$\Delta^2$-prostaglandin D derivatives of the general formula:

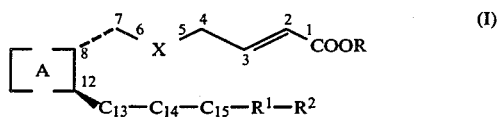

wherein

[A] represents a group of the formula:

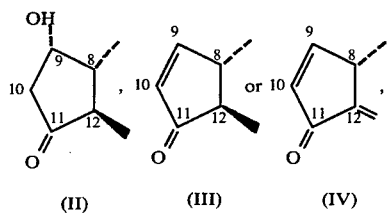

X represents an ethylene group ($-CH_2CH_2-$) or a cis-vinylene group $$(\underset{H}{\overset{\diagdown}{C}}=\underset{H}{\overset{\diagup}{C}}),$$

$C_{13}-C_{14}-C_{15}$ represents:
 (i) a group of the formula:

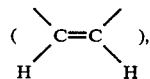

when [A] represents a group of the formula (II) or (III), or
 (ii) a group of the formula:

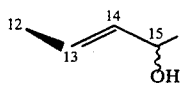

when [A] represents a group of the formula (IV), R represents a hydrogen atom or a straight-chain or branched-chain alkyl group of 1-12 carbon atoms, $R^1$ represents a single bond or a straight-chain or branched-chain alkylene group of 1-5 carbon atoms, $R^2$ represents a straight-chain or branched-chain alkyl group of 1-8 carbon atoms, a cycloalkyl group of 4-7 carbon atoms either unsubstituted or substituted by at least one straight-chain or branched-chain alkyl group of 1-8 carbon atoms or represents a phenyl group or phenoxy group either unsubstituted or substituted by at least one halogen atom, trifluoromethyl group or straight-chain or branched-chain alkyl group of 1-4 carbon atoms, the double bond between $C_2-C_3$ in formula (I) is E, the double bond between $C_9-C_{10}$ in formulae (III) and (IV) is Z, the double bond between $C_{13}-C_{14}$ in formula (V) is E, and the double bonds between $C_{12}-C_{13}$ and between $C_{14}-C_{15}$ in formula (VI), which may be in the same or different configurations, are E, Z or a mixture thereof (i.e. EZ), provided that when $R^1$ represents a single bond, $R^2$ does not represent a substituted or unsubstituted phenoxy group, and cyclodextrin clathrates thereof, and, when R represents a hydrogen atom, non-toxic salts thereof.

The compounds of the present invention include trans-$\Delta^2$-PGD derivatives of the general formula:

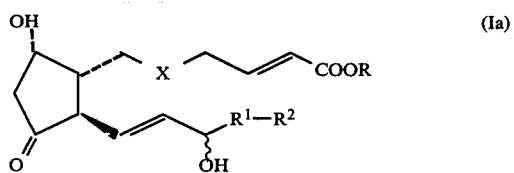

(wherein the various symbols are as hereinbefore defined), and trans-$\Delta^2$-9-deoxy-$\Delta^9$-PGD derivatives of the general formula:

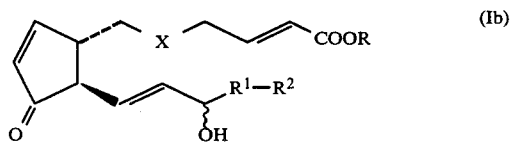

(wherein the various symbols are as hereinbefore defined), and trans-$\Delta^2$-PGD derivatives of the general formula:

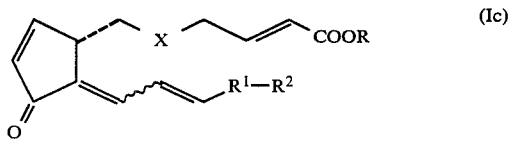

(wherein the various symbols are as hereinbefore defined).

In the compounds of the general formula (I), there are several asymmetric carbons. For example, in the compounds of the general formula (Ia), there are four asymmetric carbons (that is, carbon atoms at the 8-, 9-, 12- and 15-positions), and in the compounds of the general formula (Ib), the carbon atoms at the 8-, 12- and 15-positions are asymmetric carbons, and further in the compounds of the general formula (Ic), that at the 8-position is an asymmetric carbon. Further asymmetric carbon atoms may occur in the groups represented by R, $R^1$ and $R^2$. The presence of asymmetric carbon atoms leads to the existence of isomerism. It is to be understood that all isomers and mixtures thereof arising from the presence of asymmetric carbon atoms are to be considered within the scope of formula (I).

In the general formula (I), as the alkyl group of 1-12 carbon atoms represented by R, there may be mentioned methyl, ethyl, propyl, butyl, pentyl, hexyl, heptyl, octyl, nonyl, decyl, undecyl, and dodecyl groups and isomers thereof; R preferably represents a hydrogen atom or an alkyl group of 1-4 carbon atoms, and more especially a hydrogen atom or a methyl or ethyl group.

In the general formula (I), as the alkylene group of 1-5 carbon atoms represented by $R^1$, there may be mentioned methylene, ethylene, trimethylene, tetramethylene, pentamethylene and isomers thereof. $R^1$ preferably represents a single bond or a methylene or ethylene group [in particular a single bond or a methylene group].

In the general formula (I), as the alkyl group of 1-8 carbon atoms represented by $R^2$, there may be mentioned methyl, ethyl, propyl, butyl, pentyl, hexyl, heptyl, octyl and isomers thereof; butyl, pentyl or hexyl groups either unsubstituted or substituted by one or two methyl or ethyl groups are preferred; pentyl and hexyl unsubstituted or substituted by one or two methyl groups are especially preferred.

In the general formula (I), as the substituted or unsubstituted cycloalkyl group represented by $R^2$, there may be mentioned cyclobutyl, cyclopentyl, cyclohexyl, cycloheptyl and cyclobutyl, cyclopentyl, cyclohexyl and cycloheptyl groups substituted by one or more methyl, ethyl, propyl, butyl, pentyl, hexyl, heptyl or octyl groups; cyclobutyl, cyclopentyl or cyclohexyl groups either unsubstituted or substituted by one methyl, ethyl, propyl or butyl group are preferred; alkyl-substituted cyclopentyl is especially preferred.

In the general formula (I), as the substituted or unsubstituted phenyl or phenoxy group represented by $R^2$, there may be mentioned phenyl and phenoxy groups, and phenyl and phenoxy groups substituted by one or more atoms or groups selected from fluorine and chlorine atoms, and trifluoromethyl, methyl, ethyl, propyl or butyl groups; phenyl or phenoxy groups either unsubstituted or substituted by one chlorine atom, trifluoromethyl group, methyl group or ethyl group are preferred; chlorine is a preferred substituent.

In the general formula (I), as a preferred $R^1$-$R^2$, there may be mentioned butyl, pentyl, 1-methylpentyl, 2-methylpentyl, 3-methylpentyl, 1,1-dimethylpentyl, 1-ethylpentyl, 2-ethylpentyl, hexyl, 1-methylhexyl, 2-methylhexyl, 1-ethylhexyl, 2-ethylhexyl, heptyl, 2-methylheptyl, and 2-ethylheptyl; cyclobutyl, 1-propylcyclobutyl, 1-butylcyclobutyl, 3-ethylcyclobutyl, 3-propylcyclobutyl, cyclopentyl, cyclopentylmethyl, 2-cyclopentylethyl, 3-ethylcyclopentyl, 3-propylcyclopentyl, 3-butylcyclopentyl, cyclohexyl, cyclohexylmethyl, 2-cyclohexylethyl, 4-methylcyclohexyl, 4-ethylcyclohexyl, 4-propylcyclohexyl, and 4-butylcyclohexyl; and also benzyl, 2-phenylethyl, 4-methylbenzyl, 4-ethylbenzyl, phenoxymethyl, 2-phenoxyethyl, 3-chlorophenoxymethyl, 4-chlorophenoxymethyl, 3-trifluoromethylphenoxymethyl, 4-trifluoromethylphenoxymethyl, 4-methylphenoxymethyl and 4-ethylphenoxymethyl; pentyl, 2-methylhexyl, 3-propylcyclopentyl, benzyl and 3-chlorophenoxymethyl are especially preferred.

Further, in the general formula (I), X is preferably a cis-vinylene group, and in the general formulae (Ia) and (Ib), the preferred configuration of the hydroxyl group attached to the carbon atom at the 15-position is the α-configuration.

According to a feature of the present invention, trans-$\Delta^2$-PGD derivatives of the general formula (Ic) wherein the various symbols are as hereinbefore defined may be prepared by reacting a trans-$\Delta^2$-PGD derivative of the general formula (Ia) wherein the various symbols are as hereinbefore defined or a trans-$\Delta^2$-9-deoxy-$\Delta^9$-PGD derivative of the general formula (Ib) wherein the various symbols are as hereinbefore defined, or by reacting a compound of the general formula:

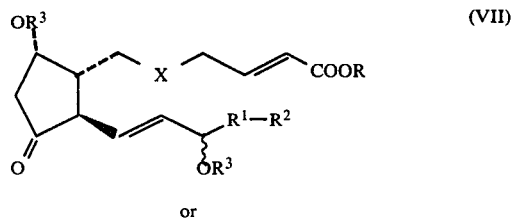

or

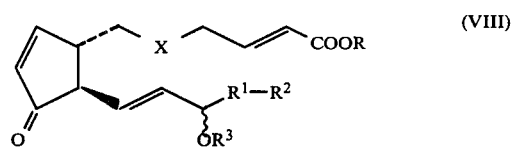

(wherein $R^3$ represents a tetrahydropyran-2-yl group, a tetrahydrofuran-2-yl group either unsubstituted or substituted by at least one alkyl group, or a 1-ethoxyethyl group, preferably a tetrahydropyran-2-yl group, and the other symbols are as hereinbefore defined) with an aqueous acid, preferably in an inert organic solvent, for example, methylene chloride, chloroform, carbon tetrachloride, diethyl ether, N,N-dimethylformamide, tetrahydrofuran or a mixture of two or more such solvents, using as the aqueous acid, for example, an aqueous solution of an inorganic acid, e.g. hydrochloric acid, hydrobromic acid, sulfuric acid or phosphoric acid or an organic acid, e.g. acetic acid, propionic acid or oxalic acid, at the reflux temperature of the solvent. The reaction is preferably carried out in tetrahydrofuran using 1N hydrochloric acid at the reflux temperature of the reaction mixture.

According to a further feature of the invention, compounds of the general formula (Ic) wherein the various symbols are as hereinbefore defined may be prepared by reacting a compound of the general formula (Ia) or (Ib), wherein the various symbols are as hereinbefore defined, with an alkylsulfonyl chloride (having 1 to 4 carbon atoms in the alkyl moiety) or arylsulfonyl chloride (the arylsulfonyl chloride is preferably a benzenesulfonyl chloride unsubstituted or substituted on the benzene ring by an alkyl group having from 1 to 4 carbon atoms), e.g. mesyl chloride or tosyl chloride, preferably in an inert organic solvent, for example, methylene chloride, in the presence of a base such as triethylamine at a low temperature, for example at a temperature of from −30° C. to 0° C.

According to a further feature of the invention trans-$\Delta^2$-PGD derivatives of the general formulae (Ia) and (Ib) wherein the various symbols are as hereinbefore defined may be prepared by hydrolyzing compounds of the general formulae (VII) and (VIII), respectively, under acidic conditions. This hydrolysis may be conducted, for example:

(1) in an aqueous solution of an organic acid such as acetic acid, propionic acid, oxalic acid or p-toluenesulfonic acid or an aqueous solution of an inorganic acid such as hydrochloric acid, sulfuric acid or phosphoric acid, suitably in the presence of a water-miscible organic solvent, for example, a lower alkanol such as methanol or ethanol (preferably methanol) or an ether such as 1,2-dimethoxyethane, dioxan or tetrahydrofuran (preferably tetrahydrofuran) at a temperature of from room temperature to 80° C., or (2) in an anhydrous lower alkanol such as methanol or ethanol in the presence of an organic acid such as p-toluenesulfonic acid or trifluoroacetic acid at a temperature of 10°–45° C.

The hydrolysis is preferably conducted using a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, or a mixture of p-toluenesulfonic acid and anhydrous methanol.

According to a further feature of the invention the trans-$\Delta^2$-9-deoxy-$\Delta^9$-PGD derivatives of the general formula (Ib) wherein the various symbols are as hereinbefore defined may also be prepared by subjecting a trans-$\Delta^2$-PGD derivative of the general formula (Ia) wherein the various symbols are as hereinbefore defined, to a mild dehydration reaction, for example, by reaction with a tris hydrochloric acid buffer solution at a temperature of 30°–40° C.

According to a further feature of the present invention, the esters of the general formula (I) wherein R represents a straight-chain or branched-chain alkyl group of 1–12 carbon atoms and the other symbols are as hereinbefore defined may also be produced by esterifying the acids of the general formula (I) wherein R represents a hydrogen atom and the other symbols are as hereinbefore defined, by known methods.

By the expression "known methods" as used in this specification and the accompanying claims is meant methods heretofore used or described in the literature.

The esterification reaction may, for example, be carried out by:
(1) a process employing a diazoalkane, or
(2) a process employing an N,N-dimethylformamide-dialkyl acetal, or
(3) a process employing a dicyclohexylcarbodiimide and an appropriate alcohol as described in Japanese Patent Specification No. 762305, or
(4) a process employing a pivaloyl halide and an appropriate alcohol as described in Japanese Patent Specification No. 756972, or
(5) a process employing an arylsulfonyl halide or an alkylsulfonyl halide and an appropriate alcohol as described in Japanese Patent Specification No. 759351.

The process employing a diazoalkane may be conducted by reaction with an appropriate diazoalkane in an inert organic solvent, for example, diethyl ether, ethyl acetate, methylene chloride, acetone or a mixture of two or more such solvents, at from −10° C. to room temperature, preferably at 0° C.

The process employing an N,N-dimethylformamide-dialkyl acetal may be conducted by reaction with an N,N-dimethylformamide-dialkyl acetal, for example, N,N-dimethylformamide-dimethyl acetal, in anhydrous benzene at from 0° C. to room temperature.

The process employing a dicyclohexylcarbodiimide may be conducted by reacting an appropriate acid and an appropriate alcohol in an inert organic solvent, for example, a halogenated hydrocarbon such as chloroform or methylene chloride, in the presence of a base such as pyridine or picoline or, preferably, 4-dimethylaminopyridine, at a temperature of 0° C. to room temperature.

The process employing a pivaloyl halide, or an arylsulfonyl halide or an alkylsulfonyl halide may be conducted by adding a tertiary amine such as triethylamine, or pyridine, and a pivaloyl halide, for example, pivaloyl chloride, or an arylsulfonyl halide, for example, benzenesulfonyl chloride or p-toluenesulfonyl chloride or an alkylsulfonyl halide, for example, methanesulfonyl chloride or ethanesulfonyl chloride either in an inert organic solvent, for example, halogenated hydrocarbons such as chloroform or methylene chloride or diethyl ether or in the absence of a solvent to form a mixed acid anhydride, and subsequently adding the appropriate alcohol and reacting at a temperature of 0° C. to room temperature.

Compounds of the general formulae (VII) and (VIII) may be prepared by oxidizing compounds of the general formulae:

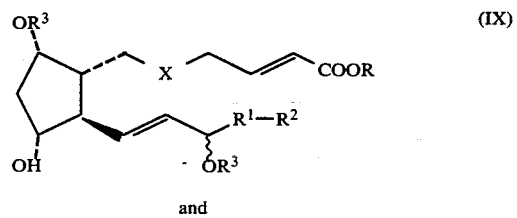

and

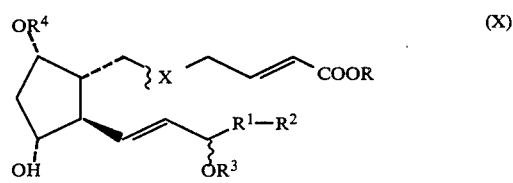

(wherein $R^4$ represents an alkylsulfonyl group, having 1 to 4 carbon atoms in the alkyl group, or a substituted or unsubstituted arylsulfonyl group, preferably a mesyl group or a tosyl group and the other symbols are as hereinbefore defined), respectively, to convert the 11-hydroxy group in the compounds of general formulae (IX) and (X) into an oxo group and, in addition to eliminate the group $OR^4$ in the compound of general formula (X) to form a double bond between $C_9$–$C_{10}$. Such an oxidation reaction is well known, and is described in detail in, for example, (a) "Synthetic Organic Chemistry III, Organic Synthesis 1", pp. 176–206 (compiled by Tetsuji Kameya and published by Nonkodo (Japan) on Aug. 1, 1976) or (b) "Compendium of Organic Synthetic Methods", vol. 1, vol. 2, and vol. 3, section 48 or 168 [published by John Wiley & Sons, Inc. (USA) in 1971, 1974, and 1977, respectively].

The oxidation is preferably carried out under mild neutral conditions using, for example, dimethylsulphide-N-chlorosuccinimide complex, thioanisole-N-chlorosuccinimide complex, dimethylsulphide-chlorine complex, thioanisole-chlorine complex [see J. Amer. Chem. Soc., 94, 7586 (1972) with respect to these complexes], dicyclohexylcarbodiimide-dimethylsulphoxide complex [see J. Amer. Chem. Soc., 87, 5661 (1965)], pyridinium chlorochromate ($C_5H_5NHCrO_3Cl$) [see Tetrahedron Letters, 2647 (1975)], sulphuric anhydride-pyridine complex [see J. Amer. Chem. Soc., 89, 5505 (1967)], chromyl chloride [see. J. Amer. Chem. Soc., 97, 5929 (1975)], chromium trioxide-pyridine complex (for example, Collins' reagent), Jones' reagent or chromic acid solution (prepared from chromium trioxide, manganese sulfate, sulfuric acid and water), or oxalyl chloride and dimethylsulfoxide (i.e. Swern oxidation); suitably the Collins oxidation, Jones oxidation or Swern oxidation may be employed. The Collins oxidation may be conducted in a halogenated hydrocarbon such as chloroform, methylene chloride or carbon tetrachloride at a temperature of from room temperature to 0° C., preferably at 0° C. The Jones oxidation is generally conducted at a temperature of not higher than room temperature. The Swern oxidation may be conducted by reaction in a halogenated hydrocarbon such as chloroform or methylene chloride at a temperature of from −50° C. to −60° C., and then treatment with triethylamine.

Starting materials of the general formulae (IX) and (X) may be prepared by the series of reactions depicted schematically below in Scheme A, wherein $R^a$ represents a straight-chain or branched-chain alkyl group of 1–4 carbon atoms, $R^5$ represents a straight-chain or branched-chain acyl group of 2–5 carbon atoms or a benzoyl group, preferably a benzoyl group, or a trisubstituted silyl group such as a trimethylsilyl, triethylsilyl, tributylsilyl, tert-butyldimethylsilyl, tribenzylsilyl or triphenylsilyl group, preferably a tert-butyldimethylsilyl group, Q represents a group —$SeC_6H_5$ or a group —$SR^6$, in which $R^6$ represents an alkyl group of 1–4 carbon atoms or a phenyl group, and the other symbols are as hereinbefore defined.

Scheme A

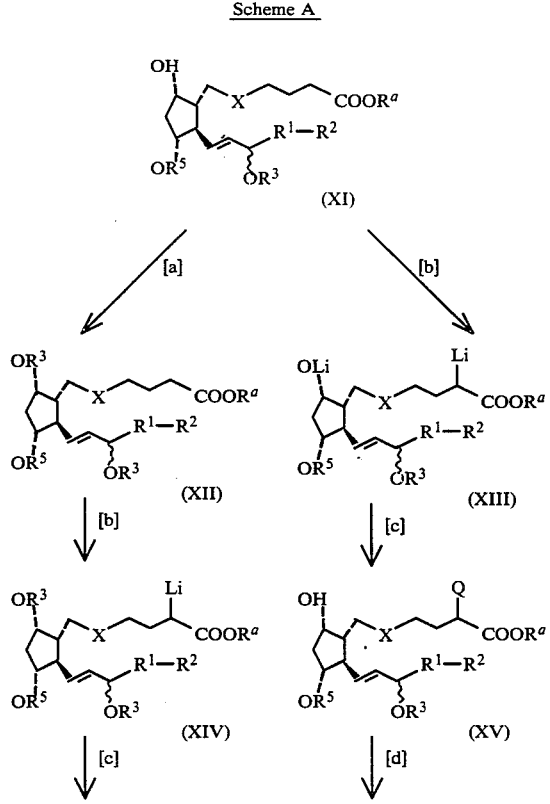

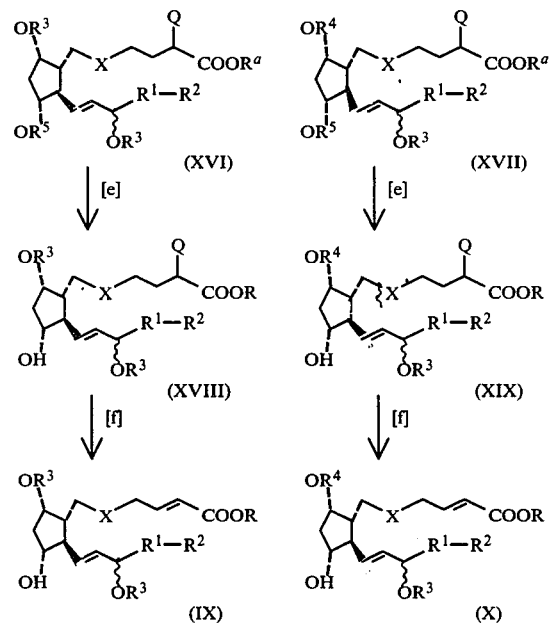

In Scheme A, each step can be effected using methods known per se. For example, the step [a] may be conducted using, e.g. 2,3-dihydropyran, 2,3-dihydrofuran or ethyl vinyl ether in an inert organic solvent, for example, methylene chloride, chloroform or diethyl ether, in the presence of a condensing agent, for example, p-toluenesulfonic acid, sulfuric acid or trifluoroacetic acid at a temperature of from room temperature to −30° C. Preferably, it is conducted using 2,3-dihydropyran in methylene chloride in the presence of pyridine p-toluenesulfonate or p-toluenesulfonic acid at room temperature.

The steps [b] may be conducted by reacting a compound of the general formula (XI) or (XII) with a lithium compound of the general formula:

$$\begin{array}{c} R^7 \\ \phantom{R^7}\diagdown \\ \phantom{RR}NLi \\ \phantom{R^7}\diagup \\ R^8 \end{array} \qquad (XX)$$

(wherein $R^7$ and $R^8$, which may be the same or different, each represent a straight-chain or branched-chain alkyl group of 1–6 carbon atoms, or a cycloalkyl group of 3–6 carbon atoms), e.g. lithium diisopropylamide.

The reaction is carried out in an organic solvent, for example, by adding dropwise a solution of a compound of general formula (XI) or (XII) in tetrahydrofuran to a solution of an amine of general formula (XX) in tetrahydrofuran at a low temperature, e.g. at −78° C., the ratio of the molecular equivalents of compounds of general formula (XI) or (XII) to (XX) in the reaction mixture being from 1:1 to 1:3. After completion of the addition of the prostaglandin solution to the amine solution, the reaction mixture is stirred at the same temperature for about 30 minutes to obtain a solution of the lithium compound of general formula (XIII) or (XIV).

The steps [c] may be conducted by reacting the lithium compound of the general formula (XIII) or (XIV), with benzeneselenenyl bromide (i.e. $C_6H_5SeBr$), or diphenyldiselenide, or a dialkyldisulphide or diphenyldisulphide of the general formula: $R^6SSR^6$, wherein $R^6$ is as hereinbefore defined, and treating the resulting intermediate with an aqueous solution to obtain the compound of the general formula (XV) or (XVI).

The reaction between the lithium compound of general formula (XIII) or (XIV) and benzeneselenenyl bromide, diphenyldiselenide or a dialkyl- or diphenyldisulphide, is preferably carried out in tetrahydrofuran, hexamethylphosphotriamide, diethyl ether, n-hexane or n-pentane or a mixture of two or more of them, tetrahydrofuran being the preferred solvent, at a low temperature, e.g. −78° C. Thus, to the lithium compound solution obtained as described above there is added a solution in tetrahydrofuran of benzeneselenenyl bromide or diphenyldiselenide in an amount of 2–4 equivalents to the lithium compound, or a dialkyl- or diphenyldisulphide in an amount of 2–3 equivalents to the lithium compound, the temperature of the two solutions being −78° C. The reaction mixture is then stirred at −78° C. (a) for one hour when a selenium compound is the reactant or (b) for 30 minutes when a disulphide is the reactant, and subsequently at ambient temperature, e.g. 15° C., for 30 minutes. After addition of an aqueous solution, for example, a small amount of a saturated aqueous ammonium chloride solution to the solution of the resulting prostaglandin intermediate to treat it, the product of formula (XV) or (XVI) is extracted with ethyl acetate.

The step [d] may be conducted by reacting with an alkylsulfonyl chloride such as mesyl chloride or an arylsulfonyl chloride such as tosyl chloride at a temperature of from −30° C. to 50° C. (i) in an inert organic solvent such as methylene chloride in the presence of a tertiary amine such as pyridine or triethylamine, or (ii) in pyridine.

The step [e] may be conducted by deacylation or desilylation. Such deacylation may be conducted by (1) using a hydroxide of an alkali metal such as lithium, sodium or potassium in an aqueous alkanol such as aqueous methanol or aqueous ethanol at a temperature of not lower than room temperature, preferably at 50°–60° C., to give compounds of general formula (XVIII) or (XIX) wherein R represents a hydrogen atom, or (2) using anhydrous potassium carbonate in an anhydrous alkanol of 1–4 carbon atoms, preferably absolute methanol, to give compounds of general formula (XVIII) or (XIX) wherein R represents a straight-chain or branched-chain alkyl group of 1–4 carbon atoms. The desilylation above is described in detail in "Protective Groups in Organic Synthesis" published by John Wiley & Sons, Inc. (USA), page 39–50 (1981) [referred to as "reference A" hereafter], and is preferably conducted by using tetrabutylammonium fluoride (n-Bu$_4$N+F−) in tetrahydrofuran at room temperature to give compounds of general formula (XVIII) or (XIX) wherein R represents a straight-chain or branched-chain alkyl groups of 1–4 carbon atoms.

If desired, acids of the general formulae (XVIII) and (XIX) may be converted into the corresponding esters by the known esterification processes hereinbefore described, and esters of the general formulae (XVIII) and (XIX) may be converted into the corresponding acids by using the conditions hereinbefore described in (1) for deacylation.

The step [f] may be conducted by treating a compound of the general formula (XVIII) or (XIX) with hydrogen peroxide or sodium periodate, and decomposing the resulting compound of the general formula:

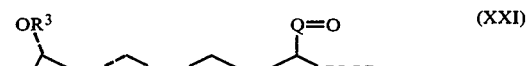   (XXI)

or

   (XXII)

(wherein the various symbols are as hereinbefore defined) to convert the grouping

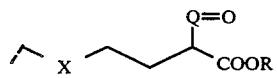

attached to the 8-position of the cyclopentane ring to a trans-$\Delta^2$ grouping

wherein R is as hereinbefore defined.

When the compound of general formula (XVIII) or (XIX) is a compound wherein Q represents —SeC$_6$H$_5$, the compound is then treated with 2 to 5 molecular equivalents of hydrogen peroxide in a mixture of ethyl acetate and tetrahydrofuran or a mixture of ethyl acetate and methanol at a temperature of 30° C. or below, or with 5 molecular equivalents of sodium periodate in the presence of a lower alkanol, preferably methanol, and water, at a temperature below 20° C., preferably for about 24 hours, to form a compound of general formula (XXI) or (XXII) wherein —Q=O represents —Se(O)C$_6$H$_5$, and stirring of the reaction mixture at a temperature of 25° to 30° C. results in decomposition of the compound to a trans-$\Delta^2$ compound of general formula (IX) or (X), which can be separated from the reaction mixture by methods known per se and, if desired, purified by column chromatography on silica gel.

When the compound of general formula (XVIII) or (XIX) is a compound wherein Q is a group —SR$^6$, R$^6$ being as hereinbefore defined, the compound is treated with hydrogen peroxide or sodium periodate in the same way as hereinbefore described for a compound of general formula (XVIII) or (XIX) wherein Q is phenylseleno to obtain a compound of general formula (XXI) or (XXII) wherein Q is a group —SR$^6$, R$^6$ being as hereinbefore defined, which can be separated from the reaction mixture by methods known per se.

When the compound of general formula (XXI) or (XXII) is one wherein Q represents an alkylthio group —SR$^{6a}$, wherein R$^{6a}$ represents an alkyl group of 1 to 4 carbon atoms, the compound is dissolved in toluene and the solution stirred preferably in the presence of a small amount of calcium carbonate, at a temperature of 100°

C. to 120° C. for a period ranging from 5 to 24 hours to decompose the compound to a trans-Δ² compound of general formula (IX) or (X). When the compound of general formula (XXI) or (XXII) is one wherein Q represents the phenylthio group, the compound is dissolved in carbon tetrachloride and the solution stirred, preferably in the presence of a small amount of calcium carbonate, at a temperature of about 50° C. for a period ranging from 5 to 24 hours to decompose the compound to a trans-Δ² compound of general formula (IX) or (X).

Compounds of general formula (XX), benzeneselenenyl bromide, diphenyldiselenide and disulphide compounds of the general formula: $R^6SSR^6$, used in Scheme A hereinbefore described, are well known per se or may be prepared by known methods, for example, by the method described in J. Amer. Chem. Soc., 95, 6139 (1973).

Starting materials of the general formula (XI) in Scheme A may be prepared by the series of reactions depicted schematically below in Scheme B, wherein $R^9$ represents a straight-chain or branched-chain alkyl group of 1-4 carbon atoms or a phenyl group, preferably a n-butyl group or a phenyl group, and the other symbols are as hereinbefore defined.

Scheme B

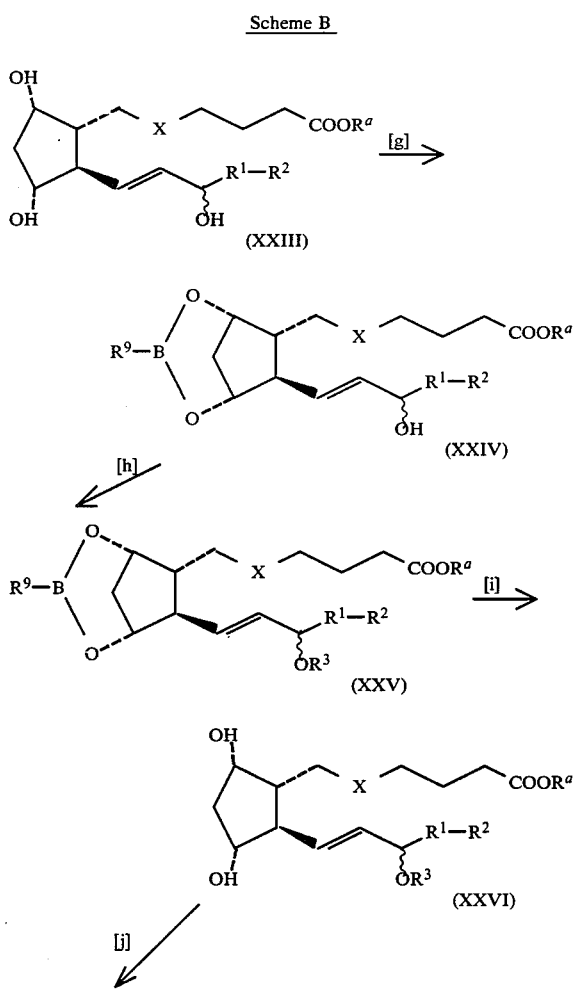

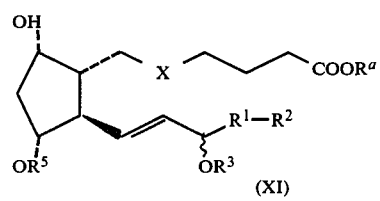

In Scheme B, each step can be effected using methods known per se. For example, the step [g] may be conducted by reacting with a boric acid corresponding to $R^9$, for example, phenylboric acid [$PhB(OH)_2$] or butylboric acid [$n\text{-}BuB(OH)_2$], in an inert organic solvent such as methylene chloride, chloroform, carbon tetrachloride or tetrahydrofuran in the presence of molecular sieves 3A or 4A at reflux temperature [see J. C. S. Chem. Comm., page 658 (1975) and Prostaglandins, vol. 9, page 109 (1975)].

The step [h] may be conducted as hereinbefore described for step [a].

The step [i] may be conducted by reacting with an aqueous hydrogen peroxide solution in an aqueous solution of an alkanol of 1-4 carbon atoms, for example, aqueous methanol or aqueous ethanol, at a temperature of not higher than 60° C., preferably at 45°-50° C.

The products of steps [g], [h] and [i] may be used without purification, in subsequent steps.

The step [j] may be conducted by selectively acylating or silylating the hydroxy group attached to the 11-position of the compound of the general formula (XXVI). Such acylation may be conducted using an appropriate acyl chloride or acid anhydride, for example, benzoyl chloride, in an inert organic solvent, for example, methylene chloride, or in the absence of a solvent in the presence of a tertiary amine such as pyridine or triethylamine at a temperature not higher than room temperature, preferably at −30° to −40° C. A suitable silylation procedure is described in detail in reference A, and may be conducted by reacting with a chlorosilane compound of the general formula: $Cl-R^{5a}$, wherein $R^{5a}$ represents a tri-substituted silyl group, in an inert organic solvent such as dimethylaminopyridine or dimethylformamide in the presence of a tertiary amine such as pyridine, imidazole or triethylamine at a temperature of from room temperature to 50° C.

In the sequence of the reaction steps illustrated by the above Scheme B, the compounds of the general formula (XXIII) employed as the starting material are known per se as PGF derivatives, and may be produced by converting the $OR^3$ groups at the 11-position and the 15-position of a compound of the general formula:

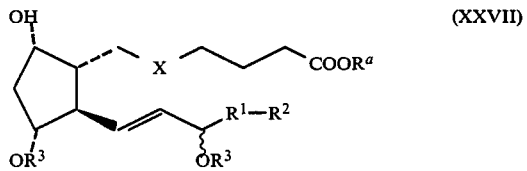

(wherein the various symbols are as hereinbefore defined) to hydroxy groups by the hydrolysis under acidic conditions hereinbefore described for the conversion of compounds of general formula (VII) or (VIII) to those of general formula (Ia) or (Ib).

Compounds of general formula (XXVII) can be obtained by the methods described in the following literature references and patent specification, or obvious modifications thereof:

(1) when the group —$R^1$—$R^2$ represents a pentyl group as described in J. Amer. Chem. Soc., 91, 5675 (1969) or ibid., 92, 397 (1970);

(2) when the group —$R^1$—$R^2$ represents an alkyl group, as described in Japanese Patent Kokai Nos. 42675/72, 54068/73, 64073/73, 124048/74, 94250/75, 96543/75 and 101340/75, British Patent Specification Nos. 1398291, 1483240 and 1540427, U.S. Pat. No. 4,024,174, and Belgian Pat. No. 850084;

(3) when $R^2$ of the group —$R^1$—$R^2$ represents a cycloalkyl group, as described in Japanese Patent Kokai Nos. 109353/74, 95250/75, 96543/75, 123647/75, 148339/75, 122040/76, 125256/76, 27753/77 and 25544/78, British Patent Specification Nos. 1464916, 1488141, 1483240, 1484210 and 1545213, U.S. Pat. Nos. 3,966,792, 4,034,003, 4,024,174, 4,045,468 and 4,087,620, and Belgian Pat. No. 844256;

(4) when $R^2$ of the group —$R^1$—$R^2$ represents a phenyl group or a phenoxy group, as described in Japanese Patent Kokai Nos. 95250/75, 96543/75, 59841/76, 101961/76 and 25745/77, British Patent Specification Nos. 1483240 and 1521747, U.S. Pat. Nos. 4,024,174 and 4,065,632, and Belgian Pat. No. 845348.

Cyclodextrin clathrates of the compounds of general formula (I) can be prepared by dissolving the cyclodextrin in water or a water-miscible organic solvent, and adding to the solution the prostaglandin derivative in a water-miscible organic solvent. The mixture is then heated and the desired cyclodextrin clathrate is isolated from the resulting solution by concentrating the mixture under reduced pressure, or by cooling and separating the product by filtration or decantation. The ratio of organic solvent to water may be varied according to the solubilities of the starting materials and products. Preferably, the temperature is not allowed to exceed 70° C. during preparation of the cyclodextrin clathrate. α-, β- or γ-Cyclodextrin, or mixtures thereof, may be used to prepare the cyclodextrin clathrates. Conversion into cyclodextrin clathrates serves to increase the stability of the prostaglandin derivatives of the general formula (I).

The prostaglandin derivatives of general formula (I) wherein R represents a hydrogen atom may, if desired, be converted by known methods into salts. Preferably the salts are non-toxic salts. By the term "non-toxic salts", as used in this specification, is meant salts the cations of which are relatively innocuous to the animal organism when used in therapeutic doses so that the beneficial pharmacological properties of the compounds of general formula (I) are not vitiated by side-effects ascribable to those cations. Preferably the salts are water-soluble. Suitable non-toxic salts include the alkali metal, e.g. sodium or potassium, salts, the alkaline earth metal, e.g. calcium or magnesium, salts and ammonium salts, and pharmaceutically acceptable, (i.e. non-toxic) amine salts. Amines suitable for forming such salts with a carboxylic acid are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms.

Suitable non-toxic amine salts are, e.g., tetraalkylammonium, such as tetramethylammonium, salts, and other organic amine salts such as methylamine salts, ethylamine salts, isopropylamine salts, tert-butylamine salts, dimethylamine salts, cyclopentylamine salts, benzylamine salts, phenethylamine salts, piperidine salts, monoethanolamine salts, diethanolamine salts, lysine salts or arginine salts.

Salts may be prepared from the acids of general formula (I) wherein R represents a hydrogen atom, by known methods, for example by reaction of stoichiometric quantities of an acid of general formula (I) and the appropriate base, e.g. an alkali metal or alkaline earth metal hydroxide or carbonate, ammonium hydroxide, ammonia or an organic amine, in a suitable solvent. The salts may be isolated by lyophilisation of the solution or, if sufficiently insoluble in the reaction medium, by filtration, if necessary, after removal of part of the solvent.

The trans-$\Delta^2$ prostaglandin D derivatives of the general formula (I), and cyclodextrin clathrates thereof, and non-toxic salts of the acids when R in the general formula (I) represents a hydrogen atom either do not show the pharmacological effects typical of other prostaglandins, for example, hypotensive activity, inhibition of platelet aggregation, stimulation of uterine muscles and the production of diarrhoea or these effects are very weak. In contrast the anti-tumour effect of the derivatives of general formula (I) is extremely strong and moreover their toxicity is extremely low. They may therefore be employed as very effective anti-tumour agents in the prevention or therapy of leukemia and solid cancer, and in treatment to produce remission thereof.

In a laboratory, in vitro test on the inhibition of proliferation of human myelogenous leukemic cells (HL-60) or on the inhibition of proliferation of cells originated from human mouth tumour (KB-cells), the compounds of the present invention showed an excellent anti-tumour effect. The experimental methods and the results are described below.

Test on the Inhibition of the Proliferation of Human Myelogenous Leukemic Cells (HL-60) Experimental method The test on the inhibition of the proliferation of human myelogenous leukemic cells was conducted by a well known method. The human myelogenous leukemic cells (HL-60) were added to an RPMI culture solution containing 10% bovine fetal serum, the number of cells in the culture solution was adjusted to $1 \times 10^5$ cells/ml, a solution in ethanol of the compound under test was added to give a concentration of 5 μg/ml or 1 μg/ml, and the mixture was subjected to stationary culture at 37° C. for 4 days. As a control, a culture solution containing 0.1% of ethanol was similarly cultured. The culture solutions were stained by the Trypan Blue staining method and the surviving cell number was measured to determine the degree of inhibition relative to the control. The results are given in the following Table.

Test on the Inhibition of the Proliferation of Cells Originated from Human Mouth Tumour (KB-cells) Experimental method The test on the inhibition of the proliferation of cells originated from human mouth tumour was conducted by a well known method. The cells originated from human mouth tumour (KB-cells) were added to an Eagle's MEM culture solution containing 10% bovine fetal serum, the number of cells in the culture solution was adjusted to $1 \times 10^5$ cells/ml, a solution in ethanol of the compound under test was added to give a concentration of 5 μg/ml or 1 μg/ml, and the mixture was subjected to stationary culture at 37° C. for 4 days. As a control, a culture solution containing 0.1% of ethanol was similarly cultured. The culture solutions were stained by the Trypan Blue staining method and the surviving cell number was measured to determine the degree of inhibition relative to the control. The results are given in the following Table.

TABLE

Inhibition of Proliferation of Human Myelogenous Leukemic Cells (HL-60) and of Cells Originated from Human Mouth Tumour (KB-cells)

| | Percent Inhibition (%) | | | |
| --- | --- | --- | --- | --- |
| | HL-60 cells | | KB-cells | |
| Compound | 5 μg/ml | 1 μg/ml | 5 μg/ml | 1 μg/ml |
| Trans-$\Delta^2$-PGD$_2$ | 19.4 | 0 | 17.9 | 2.1 |
| Trans-$\Delta^2$-9-deoxy-$\Delta^9$-PGD$_2$ | 99.0 | 1.4 | 98.5 | 9.7 |
| (2E,5Z,9Z,14EZ)-11-oxoprosta-2,5,9,12,14-pentaenoic acid | 98.3 | 4.8 | 100.0 | 0 |

On the other hand, it was confirmed that the acute toxicity of the compounds of the present invention was low, so that the trans-$\Delta^2$-PGD derivatives of the present invention may be considered to be sufficiently safe and suitable for medical use.

Preferred compounds of the general formula (I) of the present invention are, for example, as follows:

trans-$\Delta^2$-PGD$_2$,
16-methyl-trans-$\Delta^2$-PGD$_2$,
16,16-dimethyl-trans-$\Delta^2$-PGD$_2$,
17,20-dimethyl-trans-$\Delta^2$-PGD$_2$,
15-(1-butylcyclobutyl)-16,17,18,19,20-pentanor-trans-$\Delta^2$-PGD$_2$,
15-cyclopentyl-16,17,18,19,20-pentanor-trans-$\Delta^2$-PGD$_2$,
15-(3-propylcyclopentyl)-16,17,18,19,20-pentanor-trans-$\Delta^2$-PGD$_2$,
15-(4-butylcyclohexyl)-16,17,18,19,20-pentanor-trans-$\Delta^2$-PGD$_2$,
16-phenyl-17,18,19,20-tetranor-trans-$\Delta^2$-PGD$_2$,
16-phenoxy-17,18,19,20-tetranor-trans-$\Delta^2$-PGD$_2$,
16-(3-chlorophenoxy)-17,18,19,20-tetranor-trans-$\Delta^2$-PGD$_2$,
16-(3-trifluoromethylphenoxy)-17,18,19,20-tetranor-trans-$\Delta^2$-PGD$_2$,
trans-$\Delta^2$-9-deoxy-$\Delta^9$-PGD$_2$,
16-methyl-trans-$\Delta^2$-9-deoxy-$\Delta^9$-PGD$_2$,
16,16-dimethyl-trans-$\Delta^2$-9-deoxy-$\Delta^9$-PGD$_2$,
17,20-dimethyl-trans-$\Delta^2$-9-deoxy-$\Delta^9$-PGD$_2$,
15-(1-butylcyclobutyl)-16,17,18,19,20-pentanor-trans-$\Delta^2$-9-deoxy-$\Delta^9$-PGD$_2$,
15-cyclopentyl-16,17,18,19,20-pentanor-trans-$\Delta^2$-9-deoxy-$\Delta^9$-PGD$_2$,
15-(3-propylcyclopentyl)-16,17,18,19,20-pentanor-trans-$\Delta^2$-9-deoxy-$\Delta^9$-PGD$_2$,
15-(4-butylcyclohexyl)-16,17,18,19,20-pentanor-trans-$\Delta^2$-9-deoxy-$\Delta^9$-PGD$_2$,
16-phenyl-17,18,19,20-tetranor-trans-$\Delta^2$-9-deoxy-$\Delta^9$-PGD$_2$,
16-phenoxy-17,18,19,20-tetranor-trans-$\Delta^2$-9-deoxy-$\Delta^9$-PGD$_2$,
16-(3-chlorophenoxy)-17,18,19,20-tetranor-trans-$\Delta^2$-9-deoxy-$\Delta^9$-PGD$_2$,
16-(3-trifluoromethylphenoxy)-17,18,19,20-tetranor-trans-$\Delta^2$-9-deoxy-$\Delta^9$-PGD$_2$,
(2E,5Z,9Z,14EZ)-11-oxoprosta-2,5,9,12,14-pentaenoic acid,
(2E,5Z,9Z,14EZ)-11-oxo-16-methylprosta-2,5,9,12,14-pentaenoic acid,
(2E,5Z,9Z,14EZ)-11-oxo-16,16-dimethylprosta-2,5,9,12,14-pentaenoic acid,
(2E,5Z,9Z,14EZ)-11-oxo-17,20-dimethylprosta-2,5,9,12,14-pentaenoic acid,
(2E,5Z,9Z,14EZ)-11-oxo-15-(1-butylcyclobutyl)-16,17,18,19,20-pentanorprosta-2,5,9,12,14-pentaenoic acid,
(2E,5Z,9Z,14EZ)-11-oxo-15-cyclopentyl-16,17,18,19,20-pentanorprosta-2,5,9,12,14-pentaenoic acid,
(2E,5Z,9Z,14EZ)-11-oxo-15-(3-propylcyclopentyl)-16,17,18,19,20-pentanorprosta-2,5,9,12,14-pentaenoic acid,
(2E,5Z,9Z,14EZ)-11-oxo-15-(4-butylcyclohexyl)-16,17,18,19,20-pentanorprosta-2,5,9,12,14-pentaenoic acid,
(2E,5Z,9Z,14EZ)-11-oxo-16-phenyl-17,18,19,20-tetranorprosta-2,5,9,12,14-pentaenoic acid,
(2E,5Z,9Z,14EZ)-11-oxo-16-phenoxy-17,18,19,20-tetranorprosta-2,5,9,12,14-pentaenoic acid,
(2E,5Z,9Z,14EZ)-11-oxo-16-(3-chlorophenoxy)-17,18,19,20-tetranorprosta-2,5,9,12,14-pentaenoic acid,
(2E,5Z,9Z,14EZ)-11-oxo-16-(3-trifluoromethylphenoxy)-17,18,19,20-tetranorprosta-2,5,9,12,14-pentaenoic acid, and the corresponding methyl and ethyl esters, and the corresponding compounds wherein X represents an ethylene group.

The following Reference Examples and Examples illustrate the preparation of compounds of the present invention. In the Reference Examples and Examples, "TLC", "NMR", "IR" and "Mass" represent "Thin layer chromatography", "Nuclear magnetic resonance spectrum", "Infrared absorption spectrum" and "Mass spectrum", respectively. The solvents in parentheses in chromatography show the developing solvents used: ratios are by volume. Except when specified otherwise, infrared spectra were recorded by the liquid film method and nuclear magnetic resonance spectra were recorded in deuterochloroform (CDCl$_3$) solution.

REFERENCE EXAMPLE 1

(5Z,13E)-(9α,11α,15S)-9,11-Dihydroxy-15-(tetrahydropyran-2-yloxy)prosta-5,13-dienoic acid methyl ester Molecular sieve 4A (20–25 grains) was added to a solution of 1 g of PGF$_{2\alpha}$ methyl ester and 409 mg of phenylboric acid in 25 ml of dry methylene chloride, and the mixture was refluxed for one hour. The reaction mixture was cooled to room temperature and filtered. To the obtained filtrate, 0.382 ml of 2,3-dihydropyran and 70.3 mg of pyridine p-toluenesulfonate were added, and the mixture was stirred for one night. To the reaction mixture, 90 ml of ethyl acetate was added, and the resulting mixture was neutralized with a saturated aqueous solution of sodium bicarbonate, washed with a saturated aqueous solution of sodium chloride, dried over anhydrous magnesium sulfate and concentrated under reduced pressure. To a solution of the residue in 10 ml of methanol, 40 ml of water and 4 ml of a 30% aqueous hydrogen peroxide solution were added, and the reaction mixture was heated to 45°–48° C. After cooling to room temperature, the reaction mixture was concentrated under reduced pressure, and the residue was extracted with 50 ml of ethyl acetate. The extract was washed with water and a saturated aqueous solution of sodium chloride, dried over anhydrous magnesium sulfate and concentrated under reduced pressure. The residue was purified by column chromatography on silica gel using a mixed solvent of cyclohexane and ethyl acetate as an eluent to give 913 mg of the title compound having the following physical characteristics:

TLC(benzene:ethyl acetate=1:2): Rf=0.41;
NMR: $\delta$=5.63–5.16(4H, m), 4.71(1H, m), 3.66(3H, s), 4.24–3.35(5H, m), 0.88(3H, t);
IR: $\nu$=3440, 2940, 1740, 1432 cm$^{-1}$;
Mass: m/e=434, 421, 406.

The following compounds were obtained by the same procedure as described in Reference Example 1:

(a) (13E)-(9α,11α,15S)-9,11-Dihydroxy-15-(tetrahydropyran-2-yloxy)prost-13-enoic acid methyl ester
Starting material: PGF$_{1\alpha}$ methyl ester;
TLC(benzene:ethyl acetate=1:2): Rf=0.41;
NMR: $\delta$=5.7–5.3(2H, m), 4.7(1H, m), 3.6(3H, s), 4.2–3.4(5H, m), 0.9(3H, t);
IR: $\nu$=3450, 2935, 1737 cm$^{-1}$.

(b) (5Z,13E)-(9α,11α,15S,17S)-9,11-Dihydroxy-15-(tetrahydropyran-2-yloxy)-17,20-dimethylprosta-5,13-dienoic acid methyl ester
Starting material: 17S,20-dimethyl-PGF$_{2\alpha}$ methyl ester;
TLC(benzene:ethyl acetate=1:2): Rf=0.43;
NMR: $\delta$=5.7–5.2(4H, m), 4.7(1H, m), 3.6(3H, s), 4.2–3.3(5H, m), 1.0–0.8(6H, m);
IR: $\nu$=3440, 2938, 1737 cm$^{-1}$;
Mass: m/e=462.

(c) (5Z,13E)-(9α,11α,15S)-9,11-Dihydroxy-15-(tetrahydropyran-2-yloxy)-15-(3-propylcyclopentyl)-16,17,18,19,20-pentanorprosta-5,13-dienoic acid methyl ester
Starting material: 15-(3-propylcyclopentyl)-16,17,18,19,20-pentanor-PGF$_{2\alpha}$ methyl ester;
TLC(benzene:ethyl acetate=1:2): Rf=0.45;
NMR: $\delta$=5.7–5.2(4H, m), 4.7(1H, m), 3.7(3H, s), 4.2–3.3(5H, m), 0.9(3H, t);
IR: $\nu$=3440, 2935, 1735 cm$^{-1}$;
Mass: m/e=474.

(d) (5Z,13E)-(9α,11α,15S)-9,11-Dihydroxy-15-(tetrahydropyran-2-yloxy)-16-phenyl-17,18,19,20-tetranorprosta-5,13-dienoic acid methyl ester
Starting material: 16-phenyl-17,18,19,20-tetranor-PGF$_{2\alpha}$ methyl ester;
TLC(benzene:ethyl acetate=1:2): Rf=0.40;
NMR: $\delta$=7.5–7.1(5H, m), 5.7–5.2(4H, m), 4.7(1H, m), 3.6(3H, s), 4.2–3.3(5H, m);
IR: $\nu$=3350, 2937, 1737 cm$^{-1}$;
Mass: m/e=454.

(e) (5Z,13E)-(9α,11α,15R)-9,11-Dihydroxy-15-(tetrahydropyran-2-yloxy)-16-(3-chlorophenoxy)-17,18,19,20-tetranorprosta-5,13-dienoic acid methyl ester
Starting material: 16-(3-chlorophenoxy)-17,18,19,20-tetranor-PGF$_{2\alpha}$ methyl ester;
TLC(benzene:ethyl acetate=1:2): Rf=0.40;
NMR: $\delta$=7.3–6.7(4H, m), 5.7–5.2(4H, m), 4.7–3.8(8H, m), 3.7(3H, s);
IR: $\nu$=3440, 2935, 1737, 1600 cm$^{-1}$;
Mass: m/e=504.

REFERENCE EXAMPLE 2

(5Z,13E)-(9α,11α,15S)-9-Hydroxy-11-benzoyloxy-15-(tetrahydropyran-2-yloxy)prosta-5,13-dienoic acid methyl ester To a solution of 913 mg of 9,11-dihydroxy compound (prepared in Reference Example 1) in 40 ml of methylene chloride, 1.63 ml of pyridine was added. After cooling the mixture to −30° to −40° C., a solution of 0.70 ml of benzoyl chloride in 1.83 ml of methylene chloride was slowly added dropwise and then 485 μl of methanol was added. The reaction mixture was allowed to stand for 20 minutes, warmed to −20° C., 3.1 g of sodium bisulfate monohydrate was added, and the reaction mixture was warmed to room temperature and stirred for 30 minutes. To the reaction mixture, 20 ml of methylene chloride was added, washed with water and a saturated aqueous solution of sodium chloride, dried over anhydrous magnesium sulfate and concentrated under reduced pressure. The residue was purified by column chromatography on silica gel using a mixed solvent of ethyl acetate and cyclohexane as an eluent to give 942 mg of the title compound having the following physical characteristics:

TLC(cyclohexane:ethyl acetate=2:1): Rf=0.46;
NMR: $\delta$=8.1–7.8(2H, m), 7.6–7.2(3H, m), 5.8–5.2(4H, m), 5.2–4.9(1H, m), 4.5(1H, m), 3.6(3H, s), 0.85(3H, t);
IR: $\nu$=3520, 2940, 1735, 1720 cm$^{-1}$.

The following compounds were obtained by the same procedure as described in Reference Example 2:

(a) (13E)-(9α,11α,15S)-9-Hydroxy-11-benzoyloxy-15-(tetrahydropyran-2-yloxy)prost-13-enoic acid methyl ester
Starting material: 9,11-dihydroxy compound prepared in Reference Example 1(a);
TLC(cyclohexane:ethyl acetate=2:1): Rf=0.46;
NMR: $\delta$=8.1–7.8(2H, m), 7.6–7.2(3H, m), 5.8–5.2(2H, m), 5.1(1H, m), 4.6(1H, m), 3.6(3H, s), 0.88(3H, t);
IR: $\nu$=3520, 2935, 1738, 1720, 1275 cm$^{-1}$;

(b) (5Z,13E)-(9α,11α,15S,17S)-9-Hydroxy-11-benzoyloxy-15-(tetrahydropyran-2-yloxy)-17,20-dimethylprosta-5,13-dienoic acid methyl ester
Starting material: 9,11-dihydroxy compound prepared in Reference Example 1(b);
TLC(cyclohexane:ethyl acetate=2:1): Rf=0.48;
NMR: $\delta$=8.1–7.8(2H, m), 7.6–7.2(3H, m), 5.8–5.2(4H, m), 5.2–4.9(1H, m), 4.5(1H, m), 3.6(3H, s), 1.0–0.8(6H, m);
IR: $\nu$=3530, 2940, 1737, 1720, 1275 cm$^{-1}$.

(c) (5Z,13E)-(9α,11α,15S)-9-Hydroxy-11-benzoyloxy-15-(tetrahydropyran-2-yloxy)-15-(3-propylcyclopentyl)-16,17,18,19,20-pentanorprosta-5,13-dienoic acid methyl ester
Starting material: 9,11-dihydroxy compound prepared in Reference Example 1(c);
TLC(cyclohexane:ethyl acetate=2:1): Rf=0.50;
NMR: $\delta$=8.1–7.8(2H, m), 7.6–7.2(3H, m), 5.8–5.2(4H, m), 5.2–4.9(1H, m), 4.6(1H, m), 3.6(3H, s), 0.9(3H, t);
IR: $\nu$=3530, 2935, 1735, 1720 cm$^{-1}$.

(d) (5Z,13E)-(9α,11α,15S)-9-Hydroxy-11-benzoyloxy-15-(tetrahydropyran-2-yloxy)-16-phenyl-17,18,19,20-tetranorprosta-5,13-dienoic acid methyl ester Starting material: 9,11-dihydroxy compound prepared in Reference Example 1(d);
TLC(cyclohexane:ethyl acetate=2:1): Rf=0.45;
NMR: δ=8.1–7.1(10H, m), 5.8–5.2(4H, m), 5.2–4.9(1H, m), 4.6(1H, m), 3.6(3H, s);
IR: ν=3540, 2935, 1737, 1720 cm$^{-1}$.

(e) (5Z,13E)-(9α,11α,15R)-9-Hydroxy-11-benzoyloxy-15-(tetrahydropyran-2-yloxy)-16-(3-chlorophenoxy)-17,18,19,20-tetranorprosta-5,13-dienoic acid methyl ester Starting material: 9,11-dihydroxy compound prepared in Reference Example 1(e);
TLC(cyclohexane:ethyl acetate=2:1): Rf=0.45;
NMR: δ=8.1–7.8(2H, m), 7.6–6.7(7H, m), 5.8–5.2(4H, m), 5.2–4.9(1H, m), 3.7(3H, s);
IR: ν=3530, 2935, 1736, 1720, 1600, 1273 cm$^{-1}$.

REFERENCE EXAMPLE 3

(5Z,13E)-(9α,11α,15S)-9,15-Bis(tetrahydropyran-2-yloxy)-11-benzoyloxyprosta-5,13-dienoic acid methyl ester Under an atmosphere of nitrogen, 1 ml of 2,3-dihydropyran was added dropwise to a solution of 3.77 g of the 9-hydroxy compound (prepared in Reference Example 2) in 15 ml of methylene chloride at room temperature and then a trace amount of p-toluenesulfonic acid was added, and the resulting mixture was stirred for 15 minutes, 0.1 ml of triethylamine was added, and concentrated under reduced pressure. The residue was purified by column chromatography on silica gel using a mixed solvent of n-hexane and ethyl acetate as an eluent to give 3.95 g of the title compound having the following physical characteristics: TLC(n-hexane:ethyl acetate=2:1): Rf=0.45;
NMR: δ=8.1–7.9(2H, m), 7.6–7.3(3H, m), 5.7–5.3(4H, m), 5.3–5.0(1H, m), 4.7–4.4(2H, m), 3.7(3H, s), 0.8(3H, t);
IR: ν=2940, 1735, 1720, 1450 cm$^{-1}$.

The following compounds were obtained by the same procedure as described in Reference Example 3:

(a) (13E)-(9α,11α,15S)-9,15-Bis(tetrahydropyran-2-yloxy)-11-benzoyloxyprost-13-enoic acid methyl ester Starting material: 9-hydroxy compound prepared in Reference Example 2(a);
TLC(n-hexane:ethyl acetate=2:1): Rf=0.46;
NMR: δ=8.1–7.8(2H, m), 7.5–7.2(3H, m), 5.6–4.7(3H, m), 4.7–4.3(2H, m), 3.6(3H, s), 0.9(3H, t);
IR: ν=2940, 1740, 1720, 1277 cm$^{-1}$.

(b) (5Z,13E)-(9α,11α,15S,17S)-9,15-Bis(tetrahydropyran-2-yloxy)-11-benzoyloxy-17,20-dimethylprosta-5,13-dienoic acid methyl ester Starting material: 9-hydroxy compound prepared in Reference Example 2(b);
TLC(n-hexane:ethyl acetate=2:1): Rf=0.47;
NMR: δ=8.1–7.9(2H, m), 7.6–7.2(3H, m), 5.7–5.2(4H, m), 5.2–4.9(1H, m), 4.75–4.4(2H, m), 3.7(3H, s), 1.0–0.7(6H, m);
IR: ν=2940, 1736, 1720 cm$^{-1}$.

(c) (5Z,13E)-(9α,11α,15S)-9,15-Bis(tetrahydropyran-2-yloxy)-11-benzoyloxy-15-(3-propylcyclopentyl)-16,17,18,19,20-pentanorprosta-5,13-dienoic acid methyl ester Starting material: 9-hydroxy compound prepared in Reference Example 2(c);
TLC(n-hexane:ethyl acetate=2:1): Rf=0.49;
NMR: δ=8.1–7.9(2H, m), 7.6–7.2(3H, m), 5.7–5.2(4H, m), 5.3–4.9(1H, m), 4.8–4.4(2H, m), 3.7(3H, s), 0.89(3H, t);
IR: ν=2940, 1735, 1722 cm$^{-1}$.

(d) (5Z,13E)-(9α,11α,15S)-9,15-Bis(tetrahydropyran-2-yloxy)-11-benzoyloxy-16-phenyl-17,18,19,20-tetranorprosta-5,13-dienoic acid methyl ester Starting material: 9-hydroxy compound prepared in Reference Example 2(d);
TLC(n-hexane:ethyl acetate=2:1): Rf=0.45;
NMR: δ=8.1–7.1(10H, m), 5.7–5.2(4H, m), 5.2–4.9(1H, m), 4.7–4.5(2H, m), 3.7(3H, s);
IR: ν=2935, 1736, 1720 cm$^{-1}$.

(e) (5Z,13E)-(9α,11α,15R)-9,15-Bis(tetrahydropyran-2-yloxy)-11-benzoyloxy-16-(3-chlorophenoxy)-17,18,19,20-tetranorprosta-5,13-dienoic acid methyl ester Starting material: 9-hydroxy compound prepared in Reference Example 2(e);
TLC(n-hexane:ethyl acetate=2:1): Rf=0.45;
NMR: δ=8.1–7.9(2H, m), 7.6–6.7(7H, m), 5.7–5.2(4H, m), 5.2–4.9(1H, m), 3.7(3H, s);
IR: ν=2940, 1737, 1720, 1600 cm$^{-1}$.

REFERENCE EXAMPLE 4

(5Z,13E)-(9α,11α,15S)-2-phenylseleno-9,15-bis(tetrahydropyran-2-yloxy)-11-benzoyloxyprosta-5,13-dienoic acid methyl ester To a solution of 0.82 ml of diisopropylamine in 29 ml of tetrahydrofuran cooled to −78° C., 3.02 ml of a 1.68M solution of n-butyl lithium in n-hexane was added dropwise, and the solution obtained was stirred for 30 minutes at the same temperature. To the solution obtained, a solution of 2.17 g of the PGF$_{2α}$ compound (prepared in Reference Example 3) in 17 ml of tetrahydrofuran was added dropwise slowly over a period of 20 minutes at −78° C., and the solution was stirred for 30 minutes at the same temperature. To the reaction mixture, a solution of 3.16 g of diphenyl diselenide in 10 ml of tetrahydrofuran was added dropwise at −78° C. After stirring for 1 hr., the reaction mixture was poured into 100 ml of a saturated aqueous solution of ammonium chloride, and the mixture was extracted with ethyl acetate. The extract was washed successively with water and a saturated aqueous solution of sodium chloride, dried over anhydrous magnesium sulphate and then concentrated under reduced pressure. The residue was purified by column chromatography on silica gel using methylene chloride, and, subsequently, a mixture of methylene chloride and ethyl acetate as eluent to obtain 920 mg of the title compound having the following physical characteristics:
TLC (benzene:ethyl acetate=5:1): Rf=0.72;
NMR: δ=8.0–7.0 (10H, m), 5.7–4.8 (5H, m), 4.8–4.3 (2H, m), 4.3–3.0 (7H, m), 3.58 (3H, s);
IR: ν=2930, 2850, 1720, 1600 cm$^{-1}$;
Mass: m/e=712, 628, 610.

The following compounds were obtained by the same procedure as Reference Example 4:

(a) (13E)-(9α,11α,15S)-2-phenylseleno-9,15-bis-(tetrahydropyran-2-yloxy)-11-benzoyloxyprost-13-enoic acid methyl ester Starting material: PGF$_{1α}$ compound prepared in Reference Example 3(a);

TLC (benzene:ethyl acetate=5:1): Rf=0.72;
NMR: δ=8.0–7.0 (10H, m), 5.7–4.8 (3H, m), 4.8–4.4 (2H, m), 3.6 (3H, s), 0.9 (3H, t);
IR: ν=2930, 1720, 1602 cm⁻¹;
Mass: m/e=714, 630, 612.

(b) (5Z,13E)-(9α,11α,15S,17S)-2-phenylseleno-9,15-bis(tetrahydropyran-2-yloxy)-11-benzoyloxy-17,20-dimethylprosta-5,13-dienoic acid methyl ester Starting material: PGF$_{2α}$ compound prepared in Reference Example 3(b);
TLC (benzene:ethyl acetate=5:1): Rf=0.73;
NMR: δ=8.1–7.8 (2H, m) 7.7–7.1 (8H, m), 5.7–4.8 (5H, m), 4.7–4.3 (2H, m). 3.6 (3H, s), 1.0–0.8 (6H, m);
IR: ν=2930, 1720, 1280 cm⁻¹;
Mass: m/e=740, 656, 638.

(c) (5Z,13E)-(9α,11α,15S)-2-phenylseleno-9,15-bis-(tetrahydropyran-2-yloxy)-11-benzoyloxy-15-(3-propylcyclopentyl)-16,17,18,19,20-pentanorprosta-5,13-dienoic acid methyl ester Starting material: PGF$_{2α}$ compound prepared in Reference Example 3(c);
TLC (benzene:ethyl acetate=5:1): Rf=0.73;
NMR: δ=8.1–7.8 (2H, m), 7.7–7.1 (8H, m), 5.7–4.8 (5H, m), 4.7–4.3 (2H, m), 3.7 (3H, s), 0.9 (3H, t);
IR: ν=2930, 1722, 1278 cm⁻¹;
Mass: m/e=752, 668, 650.

(d) (5Z,13E)-(9α,11α,15S)-2-phenylseleno-9,15-bis-(tetrahydropyran-2-yloxy)-11-benzoyloxy-16-phenyl-17,18,19,20-tetranorprosta-5,13-dienoic acid methyl ester Starting material: PGF$_{2α}$ compound prepared in Reference Example 3(d);
TLC (benzene:ethyl acetate=5:1): Rf=0.75;
NMR: δ=8.1–7.8 (2H, m), 7.7–7.1 (13H, m), 5.7–4.8 (5H, m), 4.7–4.3 (2H, m);
IR: ν=2930, 1720 cm⁻¹;
Mass: m/e=732, 648, 630.

(e) (5Z,13E)-(9α,11α,15R)-2-phenylseleno-9,15-bis(tetrahydropyran-2-yloxy)-11-benzoyloxy-16-(3-chlorophenoxy)-17,18,19,20-tetranorprosta-5,13-dienoic acid methyl ester Starting material: PGF$_{2α}$ compound prepared in Reference Example 3(e);
TLC (benzene:ethyl acetate=5:1): Rf=0.73;
NMR: δ=8.0–6.7 (14H, m), 5.7–4.9 (5H, m), 4.8–4.4 (2H, m), 3.6 (3H, s);
IR: ν=2930, 1725, 1600 cm⁻¹;
Mass: m/e=782, 698, 680.

REFERENCE EXAMPLE 5

(5Z,13E)-(9α,11α,15S)-2-phenylseleno-9,15-bis(tetrahydropyran-2-yloxy)-11-hydroxyprosta-5,13-dienoic acid To a solution of 920 mg of ester compound (prepared in Reference Example 4) in 28 ml of methanol, 5.6 ml of a 2N aqueous solution of potassium hydroxide was added and the solution was stirred for 1.5 hr. at 50° C. The reaction mixture was adjusted to pH 2 by addition of 1N hydrochloric acid at 5° C. To the mixture, 150 ml of ice-water was added, and the mixture obtained was extracted with ethyl acetate. The extract was washed successively with water and a saturated aqueous solution of sodium chloride, dried over anhydrous magnesium sulphate, and concentrated under reduced pressure to obtain 1.03 g of crude title compound having the following physical characteristics. The product obtained was used in the procedure of Reference Example 6 without purification.

TLC (benzene:ethyl acetate=2:1): Rf=0.11;
IR: ν=3650–2400, 2930, 2850, 1715, 1695 cm⁻¹;
Mass: m/e=510, 492, 474.

The following compounds were obtained by the same procedure as Reference Example 5:

(a) (13E)-(9α,11α,15S)-2-phenylseleno-9,15-bis(tetrahydropyran-2-yloxy)-11-hydroxyprost-13-enoic acid Starting material: ester compound prepared in Reference Example 4(a);
TLC (benzene:ethyl acetate=2:1): Rf=0.12;
IR: ν=2930, 1717, 1697 cm⁻¹;
Mass: m/e=512, 494, 476

(b) (5Z,13E)-(9α,11α,15S,17S)-2-phenylseleno-9,15-bis(tetrahydropyran-2-yloxy)-11-hydroxy-17,20-dimethylprosta-5,13-dienoic acid Starting material: ester compound prepared in Reference Example 4(b);
TLC (benzene:ethyl acetate=2:1): Rf=0.13;
IR: ν=2930, 1723, 1700 cm⁻¹;
Mass: m/e=538, 520, 502.

(c) (5Z,13E)-(9α,11α,15S)-2-phenylseleno-9,15-bis-(tetrahydropyran-2-yloxy)-11-hydroxy-15-(3-propylcyclopentyl)-16,17,18,19,20-pentanorprosta-5,13-dienoic acid Starting material: ester compound prepared in Reference Example 4(c);
TLC (benzene:ethyl acetate=2:1): Rf=0.12;
IR: ν=2930, 1710 cm⁻¹;
Mass: m/e=550, 532, 514.

(d) (5Z,13E)-(9α,11α,15S)-2-phenylseleno-9,15-bis(tetrahydropyran-2-yloxy)-11-hydroxy-16-phenyl-17,18,19,20-tetranorprosta-5,13-dienoic acid Starting material: ester compound prepared in Reference Example 4(d);
TLC (benzene:ethyl acetate=2:1): Rf=0.13;
IR: ν=2930, 1725, 1700 cm⁻¹;
Mass: m/e=530, 512, 494.

(e) (5Z,13E)-(9α,11α,15R)-2-phenylseleno-9,15-bis(tetrahydropyran-2-yloxy)-11-hydroxy-16-(3-chlorophenoxy)-17,18,19,20-tetranorprosta-5,13-dienoic acid Starting material: ester compound prepared in Reference Example 4(e);
TLC (benzene:ethyl acetate=2:1): Rf=0.12;
IR: ν=2930, 1720, 1700, 1600 cm⁻¹;
Mass: m/e=580, 562, 544.

REFERENCE EXAMPLE 6

(2E,5Z,13E)-(9α,11α,15S)-9,15-bis(tetrahydropyran-2-yloxy)-11-hydroxyprosta-2,5,13-trienoic acid To a solution of 784 mg of 2-phenylseleno compound (prepared in Reference Example 5) in a mixed solvent of 3.5 ml of ethyl acetate and 3.5 ml of tetrahydrofuran, 582 mg of sodium bicarbonate was added. To the solution, 0.1 ml of a 35% aqueous solution of hydrogen peroxide was added dropwise, keeping the temperature of the reaction mixture below 30° C., and then the solution was warmed to 35° C. to start the reaction, the mixture was then immediately cooled with ice-water, and a further 0.2 ml of a 35% aqueous solution of hydrogen peroxide was added dropwise thereto. The reaction mixture was then stirred for 10 minutes at 30° C., and 200 ml of ethyl acetate was added thereto. The solution obtained was washed successively with water and a saturated aqueous solution of sodium chloride, dried over anhydrous magnesium sulphate and concentrated under reduced pressure. The residue was purified by column chromatography on silica gel using a mixture of n-hexane and ethyl acetate, and subsequently ethyl acetate as eluent to obtain 295 mg of the title compound having the following physical characteristics:

TLC (chloroform:tetrahydrofuran:acetic acid=20:2:1): Rf=0.43;
NMR: $\delta$=6.95 (1H, dt), 5.75 (1H, d), 5.9–5.0 (4H, m), 4.8–4.4 (2H, m), 4.4–3.2 (9H, m), 3.2–2.8 (2H, m);
IR: $\nu$=3600–2400, 2930, 2850, 1715, 1700, 1650 cm$^{-1}$;
Mass: m/e=418, 334, 316.

The following compounds were obtained by the same procedure as Reference Example 6:

(a) (2E,13E)-(9$\alpha$,11$\alpha$,15S)-9,15-bis(tetrahydropyran-2-yloxy)-11-hydroxyprosta-2,13-dienoic acid Starting material: phenylseleno compound prepared in Reference Example 5(a);
TLC (chloroform:tetrahydrofuran:acetic acid=20:2:1): Rf=0.43;
NMR: $\delta$=6.95 (1H, dt), 5.74 (1H, d), 5.7–5.2 (2H, m) 4.8–4.4 (2H, m), 0.9 (3H, t);
IR: $\nu$=2930, 1717, 1702, 1652 cm$^{-1}$;
Mass: m/e=420, 336, 318.

(b) (2E,5Z,13E)-(9$\alpha$,11$\alpha$,15S,17S)-9,15-bis(tetrahydropyran-2-yloxy)-11-hydroxy-17,20-dimethylprosta-2,5,13-trienoic acid Starting material: phenylseleno compound prepared in Reference Example 5(b);
TLC (chloroform:tetrahydrofuran:acetic acid=20:2:1): Rf=0.44;
NMR: $\delta$=6.9 (1H, dt), 5.9–5.2 (5H, m), 4.6 (2H, m), 1.0–0.8 (6H, m);
IR: $\nu$=2930, 1715, 1646, 1020 cm$^{-1}$;
Mass: m/e=446, 362, 344.

(c) (2E,5Z,13E)-(9$\alpha$,11$\alpha$,15S)-9,15-bis(tetrahydropyran-2-yloxy)-11-hydroxy-15-(3-propylcyclopentyl)-16,17,18,19,20-pentanorprosta-2,5,13-trienoic acid Starting material: phenylseleno compound prepared in Reference Example 5(c);
TLC (chloroform:tetrahydrofuran:acetic acid=20:2:1): Rf=0.44;
NMR: $\delta$=6.95 (1H, dt), 5.9–5.2 (5H, m), 4.6 (2H, m), 0.9 (3H, t);
IR: $\nu$=2930, 1716, 1645, 1022 cm$^{-1}$;
Mass: m/e=458, 374, 356.

(d) (2E,5Z,13E)-(9$\alpha$,11$\alpha$,15S)-9,15-bis(tetrahydropyran-2-yloxy)-11-hydroxy-16-phenyl-17,18,19,20-tetranorprosta-2,5,13-trienoic acid Starting material: phenylseleno compound prepared in Reference Example 5(d);
TLC (chloroform:tetrahydrofuran:acetic acid=20:2:1): Rf=0.44;
NMR: $\delta$=7.5–7.1 (5H, m), 6.96 (1H, dt), 5.9–5.2 (5H, m), 4.7–4.5 (2H, m);
IR: $\nu$=2930, 1714, 1644 cm$^{-1}$;
Mass: m/e=438, 354, 336.

(e) (2E,5Z,13E)-(9$\alpha$,11$\alpha$,15R)-9,15-bis(tetrahydropyran-2-yloxy)-11-hydroxy-16-(3-chlorophenoxy)-17,18,19,20-tetranorprosta-2,5,13-trienoic acid Starting material: phenylseleno compound prepared in Reference Example 5(e);
TLC (chloroform:tetrahydrofuran:acetic acid=20:2:1): Rf=0.42;
NMR: $\delta$=7.3–6.7 (5H, m), 5.77 (1H, d), 5.8–5.2 (4H, m), 4.8–4.4 (2H, m);
IR: $\nu$=2930, 1720, 1700, 1650, 1600 cm$^{-1}$;
Mass: m/e=488, 404, 386.

REFERENCE EXAMPLE 7

(2E,5Z,13E)-(9$\alpha$,15S)-9,15-bis(tetrahydropyran-2-yloxy)-11-oxoprosta-2,5,13-trienoic acid To a solution of 295 mg of 11-hydroxy compound (prepared in Reference Example 6) in 6 ml of acetone, 3.17 ml of Jones' reagent (prepared as follows: to a solution of 26.7 g of chromium trioxide in 40 ml of water, 23 ml of concentrated sulphuric acid and sufficient water was added to obtain 100 ml of Jones' reagent) was added dropwise at −30° C., and the solution was stirred for 20 minutes at the same temperature. To the solution, 0.65 ml of isopropanol was added at −30° C., and the solution was stirred for 10 minutes at the same temperature. To the reaction mixture, 100 ml of ice-water was added. The mixture was extracted with diethyl ether. The extract was washed sucessively with water and a saturated aqueous solution of sodium chloride, dried over anhydrous magnesium sulphate and concentrated under reduced pressure. The residue was purified by column chromatography on silica gel using a mixture of n-hexane and ethyl acetate as eluent to obtain 160 mg of the title compound having the following physical characteristics:

TLC (ethyl acetate): Rf=0.41;
NMR: $\delta$=6.95 (1H, dt), 5.75 (1H, d), 5.7–5.2 (4H, m), 4.7–4.35 (2H, m), 4.3–3.1 (6H, m), 3.1–2.7 (2H, m);
IR: $\nu$=3650–2400, 2930, 2850, 1730, 1710, 1695, 1640 cm$^{-1}$;
Mass: m/e=416, 332, 314.

The following compounds were obtained by the same procedure as Reference Example 7:

(a) (2E,13E)-(9$\alpha$,15S)-9,15-bis(tetrahydropyran-2-yloxy)-11-oxoprosta-2,13-dienoic acid Starting material: 11-hydroxy compound prepared in Reference Example 6(a);
TLC (ethyl acetate): Rf=0.41;
NMR: $\delta$=6.95 (1H, dt), 5.74 (1H, d), 5.6–5.3 (2H, m), 4.7–4.4 (2H, m), 0.9 (3H, t);
IR: $\nu$=2930, 1732, 1711, 1698, 1640 cm$^{-1}$
Mass: m/e=418, 334, 316.

(b) (2E,5Z,13E)-(9$\alpha$,15S,17S)-9,15-bis(tetrahydropyran-2-yloxy)-11-oxo-17,20-dimethylprosta-2,5,13-trienoic acid Starting material: 11-hydroxy compound prepared in Reference Example 6(b);
TLC (ethyl acetate): Rf=0.42;
NMR: $\delta$=6.9 (1H, dt), 5.8 (1H, d), 5.7–5.2 (4H, m), 1.0–0.8 (6H, m);
IR: $\nu$=2930, 1740, 1716, 1645 cm$^{-1}$;
Mass: m/e=444, 360, 342.

(c) (2E,5Z,13E)-(9$\alpha$,15S)-9,15-bis(tetrahydropyran-2-yloxy)-11-oxo-15-(3-propylcyclopentyl)-16,17,18,19,20-pentanorprosta-2,5,13-trienoic acid Starting material: 11-hydroxy compound prepared in Reference Example 6(c);
TLC (ethyl acetate): Rf=0.43;
NMR: $\delta$=6.95 (1H, dt), 5.77 (1H, d), 5.7–5.2 (4H, m), 4.7–4.4 (2H, m), 0.9 (3H, t);
IR: $\nu$=2930, 1738, 1715, 1645 cm$^{-1}$;
Mass: m/e=456, 372, 354.

(d) (2E,5Z,13E)-(9$\alpha$,15S)-9,15-bis(tetrahydropyran-2-yloxy)-11-oxo-16-phenyl-17,18,19,20-tetranorprosta-2,5,13-trienoic acid Starting material: 11-hydroxy compound prepared in Reference Example 6(d);
TLC (ethyl acetate): Rf=0.40;

NMR: δ=7.5-7.1 (5H, m), 6.96 (1H, dt), 5.76 (1H, d), 5.7-5.2 (4H, m), 4.7-4.4 (2H, m);
IR: ν=2930, 1735, 1717, 1698, 1643 cm$^{-1}$;
Mass: m/e=436, 352, 334.

(e) (2E,5Z,13E)-(9α,15R)-9,15-bis(tetrahydropyran-2-yloxy)-11-oxo-16-(3-chlorophenoxy)-17,18,19,20-tetranorprosta-2,5,13-trienoic acid Starting material: 11-hydroxy compound prepared in Reference Example 6(e);
TLC (ethyl acetate): Rf=0.40;
NMR: δ=7.3-6.7 (5H, m), 5.77 (1H, d), 5.7-5.2 (4H, m), 4.7-4.4 (2H, m);
IR: ν=2930, 1734, 1712, 1697, 1643, 1600 cm$^{-1}$;
Mass: m/e=486, 402, 384.

EXAMPLE 1

(2E,5Z,13E)-(9α,15S)-9,15-dihydroxy-11-oxoprosta-2,5,13-trienoic acid [i.e. trans-Δ$^2$-PGD$_2$]

To a solution of 160 mg of 9,15-bis(tetrahydropyran-2-yloxy) compound (prepared in Reference Example 7) in 0.3 ml of tetrahydrofuran, 3 ml of 65% aqueous acetic acid was added, and the solution was stirred for 8 minutes at 80° C. After addition of 100 ml of ice-water, the mixture was extracted with ethyl acetate. The extract was washed successively with water and a saturated aqueous solution of sodium chloride, and dried over anhydrous magnesium sulphate. After addition of toluene, the solution was concentrated under reduced pressure at low temperature. The residue was purified by column chromatography on silica gel using a mixture of n-hexane and ethyl acetate and, subsequently, ethyl acetate, as eluent to obtain 41 mg of the title compound having the following physical characteristics:
TLC (chloroform:tetrahydrofuran:acetic acid=10:2:1): Rf=0.28;
NMR: δ=7.07 (1H, dt), 5.87 (1H, d), 5.65 (1H, dd), 5.44 (1H, dd), 5.7-5.4 (2H, m), 4.55-4.4 (1H, m), 4.11 (1H, dt), 3.1-3.0 (2H, m), 2.85 (1H, dd), 0.88 (3H, t);
IR: ν=3650-2400, 2930, 2850, 1720, 1690, 1640 cm$^{-1}$;
Mass: m/e=332, 314, 243.

The following compounds were obtained by the same procedure as Example 1:

(a) (2E,13E)-(9α,15S)-9,15-dihydroxy-11-oxoprosta-2,13-dienoic acid [i.e. trans-Δ$^2$-PGD$_1$]

Starting material: 9,15-bis(tetrahydropyran-2-yloxy) compound prepared in Reference Example 7(a);
TLC (chloroform:tetrahydrofuran:acetic acid=10:2:1): Rf=0.28;
NMR: δ=7.05 (1H, dt), 5.85 (1H, d), 5.7-5.4 (2H, m), 4.50 (1H, m), 4.10 (1H, m), 0.88 (3H, t);
IR: ν=3400, 2930, 1722, 1693, 1641 cm$^{-1}$;
Mass: m/e=334, 316.

(b) (2E,5Z,13E)-(9α,15S,17S)-9,15-dihydroxy-11-oxo-17,20-dimethylprosta-2,5,13-trienoic acid [i.e. 17S,20-dimethyl-trans-Δ$^2$-PGD$_2$]

Starting material: 9,15-bis(tetrahydropyran-2-yloxy) compound prepared in Reference Example 7(b);
TLC (chloroform:tetrahydrofuran:acetic acid=10:2:1): Rf=0.29;
NMR: δ=7.07 (1H, dt), 5.87 (1H, d), 5.75-5.35 (4H, m), 4.48 (1H, m), 4.12 (1H, m), 1.00-0.90 (6H, m);
IR: ν=3400, 2930, 1725, 1695, 1645 cm$^{-1}$;
Mass: m/e=360, 342.

(c) (2E,5Z,13E)-(9α,15S)-9,15-dihydroxy-11-oxo-15-(3-propylcyclopentyl)-16,17,18,19,20-pentanorprosta-2,5,13-trienoic acid [i.e. 15-(3-propylcyclopentyl)-16,17,18,19,20-pentanor-trans-Δ$^2$-PGD$_2$]

Starting material: 9,15-bis(tetrahydropyran-2-yloxy) compound prepared in Reference Example 7 (c);
TLC (chloroform:tetrahydrofuran:acetic acid=10:2:1): Rf=0.29;
NMR: δ=7.07 (1H, dt), 5.87 (1H, d), 5.76-5.34 (4H, m), 4.47 (1H, m), 4.11 (1H, m), 0.88 (3H, t);
IR: ν=3410, 2930, 1726, 1696, 1646 cm$^{-1}$;
Mass: m/e=372, 354.

(d) (2E,5Z,13E)-(9α,15S)-9,15-dihydroxy-11-oxo-16-phenyl-17,18,19,20-tetranorprosta-2,5,13-trienoic acid [i.e. 16-phenyl-17,18,19,20-tetranor-trans-Δ$^2$-PGD$_2$]

Starting material: 9,15-bis(tetrahydropyran-2-yloxy) compound prepared in Reference Example 7 (d);
TLC (chloroform:tetrahydrofuran:acetic acid=10:2:1): Rf=0.27;
NMR: δ=7.5-7.0 (6H, m), 5.88 (1H, d), 5.76-5.34 (4H, m), 4.49 (1H, m);
IR: ν=3410, 2930, 1730, 1692, 1642 cm$^{-1}$;
Mass: m/e=352, 334.

(e) (2E,5Z,13E)-(9α,15R)-9,15-dihydroxy-11-oxo-16-(3-chlorophenoxy)-17,18,19,20-tetranorprosta-2,5,13-trienoic acid [i.e. 16-(3-chlorophenoxy)-17,18,19,20-tetranor-trans-Δ$^2$-PGD$_2$]

Starting material: 9,15-bis(tetrahydropyran-2-yloxy) compound prepared in Reference Example 7 (e);
TLC (chloroform:tetrahydrofuran:acetic acid=10:2:1): Rf=0.27
NMR: δ=7.3-6.7 (5H, m), 5.88 (1H, d), 5.77-5.36 (4H, m), 4.65-4.3 (2H, m), 3.93 (2H, d);
IR: ν=3430, 2930, 1723, 1693, 1643, 1600 cm$^{-1}$;
Mass: m/e=402, 384.

EXAMPLE 2

(2E,5Z,13E)-(9α,15S)-9,15-dihydroxy-11-oxoprosta-2,5,13-trienoic acid ethyl ester [i.e. trans-Δ$^2$-PGD$_2$ ethyl ester]

To solution of 50 mg of trans-Δ$^2$-PGD$_2$ (prepared in Example 1) in 0.5 ml of ethanol, 29 mg of dicyclohexylcarbodiimide was added at 0° C. To the solution obtained, a solution of 17 mg of 4-dimethylaminopyridine in 2.5 ml of methylene chloride was added dropwise slowly at the same temperature. After warming to room temperature, the solution was stirred for 2 hrs. To the resulting solution, 14.5 mg of dicyclohexylcarbodiimide was added, and the solution was stirred for 1 hr. The reaction mixture was diluted with diethyl ether, washed with water, dried over anhydrous magnesium sulphate and concentrated under reduced pressure. The residue was purified by column chromatography on silica gel using a mixture of diethyl ether and n-hexane, and, subsequently, diethyl ether, as eluent to obtain 16 mg of the title compound having the following physical characteristics:
TLC (chloroform:tetrahydrofuran:acetic acid=10:2:1): Rf=0.49;
NMR: δ=7.07 (1H, dt), 5.86 (1H, d), 5.75-5.35 (4H, m), 4.48 (1H, m), 4.13 (2H, q), 4.20-4.00 (1H, m) 1.25 (3H, t), 0.88 (3H, t);
Mass: m/e=360, 342.

The following compounds were obtained by the same procedure as Example 2:

(a) (2E,13E)-(9α,15S)-9,15-dihydroxy-11-oxoprosta-2,13-dienoic acid ethyl ester [i.e. trans-Δ$^2$-PGD$_1$ ethyl ester]

Starting material: trans-$\Delta^2$-PGD$_1$ prepared in Example 1 (a);

TLC (chloroform:tetrahydrofuran:acetic acid=10:2:1): Rf=0.49;

NMR: $\delta$=7.05 (1H, dt), 5.86 (1H, d), 5.70–5.40 (2H, m), 4.45 (1H, m), 4.20–4.00 (3H, m), 0.88 (3H, t);

Mass: m/e=362, 344.

EXAMPLE 3

(2E,5Z,9Z,13E)-(15S)-11-oxo-15-hydroxyprosta-2,5,9,13-tetraenoic acid [i.e. trans-$\Delta^2$-9-deoxy-$\Delta^9$-PGD$_2$]

To a solution of 16 mg of PGD$_2$ compound (prepared in Example 1) in 0.23 ml of ethanol, 23 ml of trishydrochloric acid buffer solution (pH 7.2; prepared from 17.5 ml of a 0.2M aqueous solution of tris(hydroxymethyl)aminomethane, 31.5 ml of 0.1N hydrochloric acid and 21 ml of water) was added, and the solution was stirred for 30 hrs. at 37° C. The reaction mixture was adjusted to pH 2 by addition of 1N hydrochloric acid, cooling the mixture with an ice bath. After addition of ice-water, the mixture was extracted with ethyl acetate. The extract was washed successively with water and a saturated aqueous solution of sodium chloride, dried over anhydrous magnesium sulphate, and concentrated under reduced pressure. The residue was purified by column chromatography on silica gel using a mixture of n-hexane and ethyl acetate as eluent to obtain 1.6 mg of the title compound having the following physical characteristics:

TLC (chloroform:tetrahydrofuran:acetic acid=10:2:1): Rf=0.64;

NMR: $\delta$=7.58 (1H, dd), 7.03 (1H, dt), 6.19 (1H, dd), 5.84 (1H, d), 5.75–5.4 (4H, m), 4.10 (1H, dt), 2.54–2.42 (2H, m), 0.88 (3H, t);

Mass: m/e=322(M+), 314, 243.

The following compounds were obtained by the same procedure as Example 3:

(a) (2E,9Z,13E)-(15S)-11-oxo-15-hydroxyprosta-2,9,13-trienoic acid [i.e. trans-$\Delta^2$-9-deoxy-$\Delta^9$-PGD$_1$]

Starting material: PGD$_1$ compound prepared in Example 1 (a);

TLC (chloroform:tetrahydrofuran:acetic acid=10:2:1): Rf=0.64;

NMR:$\delta$=7.57 (1H, dd), 7.02 (1H, dt), 6.19 (1H, dd), 5.83 (1H, d), 5.7–5.4 (2H, m), 4.10 (1H, dt), 0.88 (3H, t);

Mass: m/e=344(M+), 316.

(b) (2E,5Z,9Z,13E)-(15S,17S)-11-oxo-15-hydroxy-17,20-dimethylprosta-2,5,9,13-tetraenoic acid [i.e. 17S,20-dimethyl-trans-$\Delta^2$-9-deoxy-$\Delta^9$-PGD$_2$]

Starting material: PGD$_2$ compound prepared in Example 1 (b);

TLC (chloroform:tetrahydrofuran:acetic acid=10:2:1): Rf=0.65;

NMR: $\delta$=7.58 (1H, dd), 7.04 (1H, dt), 6.19 (1H, dd), 5.84 (1H, d), 5.75–5.40 (4H, m), 4.10 (1H, m), 1.00–0.90 (6H, m);

Mass: m/e=360(M+), 342.

(c) (2E,5Z,9Z,13E)-(15S)-11-oxo-15-hydroxy-15-(3-propylcyclopentyl)-16,17,18,19,20-pentanorprosta-2,5,9,13-tetraenoic acid [i.e. 15-(3-propylcyclopentyl)-16,17,18,19,20-pentanor-trans-$\Delta^2$-9-deoxy-$\Delta^9$-PGD$_2$]

Starting material: PGD$_2$ compound prepared in Example 1 (c);

TLC (chloroform:tetrahydrofuran:acetic acid=10:2:1): Rf=0.66;

NMR: $\delta$=7.58 (1H, dd), 7.02 (1H, dt), 6.18 (1H, dd), 5.84 (1H, d), 5.76–5.42 (4H, m), 4.11 (1H, m), 0.88 (3H, t);

Mass: m/e=372(M+), 354.

(d) (2E,5Z,9Z,13E)-(15S)-11-oxo-15-hydroxy-16-phenyl-17,18,19,20-tetranorprosta-2,5,9,13-tetraenoic acid [i.e. 16-phenyl-17,18,19,20-tetranor-trans-$\Delta^2$-9-deoxy-$\Delta^9$-PGD$_2$]

Starting material: PGD$_2$ compound prepared in Example 1 (d);

TLC (chloroform:tetrahydrofuran:acetic acid=10:2:1): Rf=0.62;

NMR: $\delta$=7.58 (1H, dd), 7.5–6.97 (6H, m), 6.20 (1H, dd), 5.85 (1H, d), 5.75–5.40 (4H, m);

Mass: m/e=352(M+), 334.

(e) (2E,5Z,9Z,13E)-(15R)-11-oxo-15-hydroxy-16-(3-chlorophenoxy)-17,18,19,20-tetranorprosta-2,5,9,13-tetraenoic acid [i.e. 16-(3-chlorophenoxy)-17,18,19,20-tetranor-trans-$\Delta^2$-9-deoxy-66$^9$-PGD$_2$]

Starting material: PGD$_2$ compound prepared in Example 1 (e);

TLC (chloroform:tetrahydrofuran:acetic acid=10:2:1): Rf=0.62;

NMR: $\delta$=7.60 (1H, dd), 7.3–6.7 (6H, m), 6.20 (1H, dd), 5.74–5.30 (4H, m), 4.55 (1H, m), 4.03 (2H, d);

Mass: m/e=402(M+), 384.

(f) (2E,5Z,9Z,13E)-(15S)-11-oxo-15-hydroxyprosta-2,5,9,13-tetraenoic acid ethyl ester [i.e. trans-$\Delta^2$-9-deoxy-$\Delta^9$-PGD$_2$ ethyl ester]

Starting material: PGD$_2$ ester compound prepared in Example 2;

NMR: $\delta$=7.58 (1H, dd), 7.03 (1H, dt), 6.19 (1H, dd), 5.84 (1H, d), 5.75–5.40 (4H, m), 4.10 (3H, m), 0.88 (3H, t);

Mass: m/e=360(M+), 342.

(g) (2E,9Z,13E)-(15S)-1-oxo-15-hydroxyprosta-2,9,13-trienoic acid ethyl ester [i.e. trans-$\Delta^2$-9-deoxy-$\Delta^9$-PGD$_1$ ethyl ester]

Starting material: PGD$_1$ ester compound prepared in Example 2 (a);

NMR: $\delta$=7.56 (1H, dd), 7.03 (1H, dt), 6.20 (1H, dd), 5.82 (1H, d), 5.70–5.40 (2H, m), 4.10 (3H, m), 0.88 (3H, t);

Mass: m/e=362(M+), 344.

EXAMPLE 4

(2E,5Z,9Z,14EZ)-11-oxoprosta-2,5,9,12,14-pentaenoic acid

To a solution of 11 mg of PGD$_2$ compound (prepared in Example 1) in 0.3 ml of tetrahydrofuran, 0.3 ml of 1N hydrochloric acid was added, and the solution was refluxed for 1 hr. To the reaction mixture, 100 ml of ice-water was added. The mixture was extracted with ethyl acetate, and the extract was washed successively with water and a saturated aqueous solution of sodium chloride, dried over anhydrous magnesium sulphate, and concentrated under reduced pressure. The residue was purified by column chromatography on silica gel using a mixture of n-hexane and ethyl acetate as eluent, to obtain 3.18 mg of the title compound having the following physical characteristics:

TLC (chloroform:tetrahydrofuran:acetic acid=10:2:1): Rf=0.81;

NMR: $\delta$=7.45 (1H, dd), 6.99 (1H, dt), 7.0–6.9 (1H, m), 6.38 (1H, dd), 6.45–6.2 (2H, m), 5.80 (1H, d), 5.6–5.4 (2H, m), 3.7–3.5 (1H, m), 3.0–2.85 (2H, m);

IR: $\nu$=3650–2400, 2930, 2860, 1710, 1690, 1620 cm$^{-1}$;

Mass: m/e=314(M+), 243.

The following compounds were obtained by the same procedure as Example 4:

(a) (2E,9Z,14EZ)-11-oxoprosta-2,9,12,14-tetraenoic acid

Starting material: PGD$_1$ compound prepared in Example 1 (a);

TLC (chloroform:tetrahydrofuran:acetic acid=10:2:1): Rf=0.81;

NMR: $\delta$=7.44 (1H, dd), 6.98 (1H, dt), 7.0–6.9 (1H, m), 6.45–6.20 (3H, m), 5.80 (1H, d), 0.88 (3H, t);

IR: $\nu$=2930, 1692, 1622 cm$^{-1}$;

Mass: m/e=316(M+).

(b) (2E,5Z,9Z,14EZ)-(17S)-11-oxo-17,20-dimethylprosta-2,5,9,12,14-pentaenoic acid Starting material: PGD$_2$ compound prepared in Example 1 (b);

TLC (chloroform:tetrahydrofuran:acetic acid=10:2:1): Rf=0.82;

NMR: $\delta$=7.45 (1H, dd), 6.99 (1H, dt), 7.00–6.93 (1H, m), 6.45–6.23 (3H, m), 5.80 (1H, d), 5.60–5.40 (2H, m), 1.00–0.90 (6H, m);

IR: $\nu$=2930, 1692, 1623 cm$^{-1}$;

Mass: m/e=342(M+).

(c) (2E,5Z,9Z,14EZ)-11-oxo-15-(3-propylcyclopentyl)-16,17,18,19,20-pentanorprosta-2,5,9,12,14-pentaenoic acid Starting material: PGD$_2$ compound prepared in Example 1 (c);

TLC (chloroform:tetrahydrofuran:acetic acid=10:2:1): Rf=0.81;

NMR: $\delta$=7.46 (1H, dd), 6.98 (1H, dt), 7.00–6.91 (1H, m), 6.38 (1H, dd), 6.45–6.15 (2H, m), 5.81 (1H, d), 5.60–5.40 (2H, m), 0.88 (3H, t);

IR: $\nu$=2930, 1693, 1624 cm$^{-1}$;

Mass: m/e=354(M+).

(d) (2E,5Z,9Z,14EZ)-11-oxo-16-phenyl-17,18,19,20-tetranorprosta-2,5,9,12,14-pentaenoic acid Starting material: PGD$_2$ compound prepared in Example 1 (d);

TLC (chloroform:tetrahydrofuran:acetic acid=10:2:1): Rf=0.80;

NMR: $\delta$=7.5–6.9 (8H, m), 6.45–6.20 (3H, m), 5.81 (1H, d), 5.6–5.4 (2H, m);

IR: $\nu$=2930, 1697, 1622 cm$^{-1}$;

Mass: m/e=334(M+).

(e) (2E,5Z,9Z,14EZ)-11-oxo-16-(3-chlorophenoxy)-17,18,19,20-tetranorprosta-2,5,9,12,14-pentaenoic acid Starting material: PGD$_2$ compound prepared in Example 1 (e);

TLC (chloroform:tetrahydrofuran:acetic acid=10:2:1): Rf=0.80;

NMR: $\delta$=7.47 (1H, dd), 7.3–6.7 (5H, m), 6.46–6.22 (3H, m), 5.81 (1H, d), 5.6–5.4 (2H, m);

IR: $\nu$=2930, 1730, 1697, 1622, 1600 cm$^{-1}$;

Mass: m/e=384(M+).

(f) (2E,5Z,9Z,14EZ)-11-oxoprosta-2,5,9,12,14-pentaenoic acid ethyl ester

Starting material: PGD$_2$ ester compound prepared in Example 2;

NMR: $\delta$=7.45 (1H, dd), 6.98 (1H, dt), 6.45–6.20 (3H, m), 5.80 (1H, d), 5.60–5.40 (2H, m), 4.10 (2H, q), 0.90 (3H, t);

Mass: m/e=342 (M+).

(g) (2E,9Z,14EZ)-11-oxoprosta-2,9,12,14-tetraenoic acid ethyl ester

Starting material: PGD$_1$ ester compound prepared in Example 2 (a);

NMR: $\delta$=7.45 (1H, dd), 6.97 (1H, dt), 6.45–6.20 (3H, m), 5.80 (1H, d), 4.10 (2H, q), 0.90 (3H, t);

Mass: m/e=344(M+).

The present invention includes within its scope pharmaceutical compositions which comprise at least one trans-$\Delta^2$ prostaglandin D derivative of general formula (I), cyclodextrin clathrate thereof or, when R represents a hydrogen atom, non-toxic salt thereof together with a pharmaceutical carrier or coating.

In clinical practice, for the prevention or the therapy (including therapy to secure remission) against leukemia or solid cancer, the compounds of the present invention will normally be administered systemically or partially; usually by oral or parenteral (e.g. intraveous, subcutaneous or intramuscular) administration.

Solid compositions for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorbable material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations according to the invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark). These compositions may also include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administraion. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, body weight, symptoms, the desired therapeutic effects, the route of administration, and the duration of the treatment.

In the human adult, the doses per person are generally between 5 mg and 500 mg by oral administration, and between 500 μg and 50 mg by parenteral administration, preferably intravenous administration, for the prevention or the therapy (including therapy to secure remission) against leukemia or solid cancer, and can be administered up to several times per day.

As mentioned above, the doses to be used depend on various conditions. Therefore, there may be cases in which doses greater than the ranges specified above, or lower than the ranges specified above, may be used.

The following Examples illustrate pharmaceutical compositions according to the invention.

EXAMPLE 5

A solution of one gram of trans-$\Delta^2$-9-deoxy-$\Delta^9$-PGD$_2$ in 5 ml of ethanol was well mixed with 5 g of microcrystalline cellulose. After drying the mixture sufficiently, 100 mg of magnesium stearate, 20 mg of silicon dioxide, 10 mg of talc, 200 mg of cellulose calcium gluconate (CCG) and further microcrystalline cellulose to produce 10 g of mixture were added. After mixing well to ensure homogeneity the mixture was punched out in conventional manner to obtain 100 tablets each containing 10 mg of the active ingredient.

EXAMPLE 6

A α-cyclodextrin and β-cyclodextrin clathrate of trans-$\Delta^2$-9-deoxy-$\Delta^9$-PGD$_2$ [prepared by dissolving 2.4 g of α-cyclodextrin and one g of β-cyclodextrin in 300 ml of water, adding thereto 100 mg of trans-$\Delta^2$-9-deoxy-$\Delta^9$-PGD$_2$, stirring well and then concentrating under reduced pressure] was dissolved in 150 ml of distilled water for injection. The solution was sterilized by filtration in conventional manner, placed in 1.5 ml portions in 5 ml ampoules and freeze-dried to obtain 100 ampoules of solid composition for injection each containing 1 mg of the active ingredient.

We claim:

1. A trans-$\Delta^2$-prostaglandin D derivative of the formula:

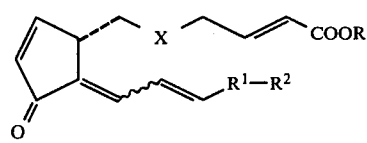

(Ic)

wherein X represents an ethylene group (—CH$_2$CH$_2$—) or a cis-vinylene group

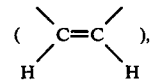

R represents a hydrogen atom or a straight-chain or branched-chain alkyl group of 1–12 carbon atoms, R$^1$ represents a single bond or a straight-chain or branched-chain alkylene group of 1–5 carbon atoms, R$^2$ represents a straight-chain or branched-chain alkyl group of 1–8 carbon atoms, a cycloalkyl group of 4–7 carbon atoms either unsubstituted or substituted by at least one straight-chain or branched-chain alkyl group of 1–8 carbon atoms or represents a phenyl group or phenoxy group either unsubstituted or substituted by at least one halogen atom, trifluoromethyl group or straight-chain or branched-chain alkyl group of 1–4 carbon atoms, the double bond between C$_2$–C$_3$ is E, the double bond between C$_9$–C$_{10}$ is Z, and the double bonds between C$_{12}$–C$_{13}$ and between C$_{14}$–C$_{15}$, which may be in the same or different configurations, are E, Z or a mixture thereof, provided that when R$^1$ represents a single bond, R$^2$ does not represent a substituted or unsubstituted phenoxy group, or a cyclodextrin clathrate thereof, or, when R represents a hydrogen atom, a non-toxic salt thereof.

2. A prostaglandin derivative according to claim 1, wherein R represents a hydrogen atom or a straight-chain or branched-chain alkyl group of 1–4 carbon atoms.

3. A prostaglandin derivative according to claim 1, wherein X represents a cis-vinylene group.

4. A prostaglandin derivative according to claim 1, wherein X represents an ethylene group.

5. A prostaglandin derivative according to claim 1, wherein R$^2$ represents a straight-chain or branched-chain alkyl group of 1–8 carbon atoms.

6. A prostaglandin derivative according to claim 1, wherein R$^1$–R$^2$ represents a butyl, pentyl, 1-methylpentyl, 2-methylpentyl, 3-methylpentyl, 1,1-dimethylpentyl, 1-ethylpentyl, 2-ethylpentyl, hexyl, 1-methylhexyl, 2-methylhexyl, 1-ethylhexyl, 2-ethylhexyl, heptyl, 2-methylheptyl or 2-ethylheptyl group.

7. A prostaglandin derivative according to claim 6, which is (2E,9Z,14EZ)-11-oxoprosta-2,9,12,14-tetraenoic acid, or its ethyl ester or a cyclodextrin clathrate thereof, or a non-toxic salt of a said acid.

8. A prostaglandin derivative according to claim 6, which is (2E,5Z,9Z,14EZ)-11-oxoprosta-2,5,9,12,14-pentaenoic acid, or its ethyl ester or a cyclodextrin clathrate thereof, or a non-toxic salt of a said acid.

9. A prostaglandin derivative according to claim 6, which is (2E,5Z,9Z,14EZ)-(17S)-11-oxo-17,20-dimethylprosta-2,5,9,12,14-pentaenoic acid or a cyclodextrin clathrate or non-toxic salt thereof.

10. A prostaglandin derivative according to claim 1, wherein R$^2$ represents a cycloalkyl group of 4–7 carbon atoms either unsubstituted or substituted by at least one straight-chain or branched-chain alkyl group of 1–8 carbon atoms.

11. A prostaglandin derivative according to claim 1, wherein $R^1$–$R^2$ represents a cyclobutyl, 1-propylcyclobutyl, 1-butylcyclobutyl, 3-ethylcyclobutyl, 3-propylcyclobutyl, cyclopentyl, cyclopentylmethyl, 2-cyclopentylethyl, 3-ethylcyclopentyl, 3-propylcyclopentyl, 3-butylcyclopentyl, cyclohexyl, cyclohexylmethyl, 2-cyclohexylethyl, 4-methylcyclohexyl, 4-ethylcyclohexyl, 4-propylcyclohexyl or 4-butylcyclohexyl group.

12. A prostaglandin derivative according to claim 11, which is (2E,5Z,9Z,14EZ)-11-oxo-15-(3-propylcyclopentyl)-16,17,18,19,20-pentanorprosta-2,5,9,12,14-pentaenoic acid or a cyclodextrin clathrate or non-toxic salt thereof.

13. A prostaglandin derivative according to claim 1, wherein $R^2$ represents a phenyl group or phenoxy group either unsubstituted or substituted by at least one halogen atom, trifluoromethyl group or straight-chain or branched-chain alkyl group of 1–4 carbon atoms.

14. A prostaglandin derivative according to claim 1, wherein $R^1$–$R^2$ represents a benzyl, 2-phenylethyl, 4-methylbenzyl, 4-ethylbenzyl, phenoxymethyl, 2-phenoxyethyl, 3-chlorophenoxymethyl, 4-chlorophenoxymethyl, 3-trifluoromethylphenoxymethyl, 4-trifluoromethylphenoxymethyl, 4-methylphenoxymethyl or 4-ethylphenoxymethyl group.

15. A prostaglandin derivative according to claim 14, which is (2E,5Z,9Z,14EZ)-11-oxo-16-phenyl-17,18,19,20-tetranorprosta-2,5,9,12,14-pentaenoic acid or a cyclodextrin clathrate or non-toxic salt thereof.

16. A prostaglandin derivative according to claim 14, which is (2E,5Z,9Z,14EZ)-11-oxo-16-(3-chlorophenoxy)-17,18,19,20-tetranorprosta-2,5,9,12,14-pentaenoic acid or a cyclodextrin clathrate or non-toxic salt thereof.

17. An alkyl ester according to claim 18 which is a methyl or ethyl ester.

18. An alkyl ester containing 1 to 4 carbon atoms in the alkyl group of a prostaglandin derivative according to claim 1 selected from the group consisting of (2E,9Z,14EZ)-11-oxoprosta-2,9,12,14-tetraenoic acid, (2E,5Z,9Z,14EZ)-11-oxoprosta-2,5,9,12,14-pentaenoic acid, (2E,5Z,9Z,14EZ)-(17S)-11-oxo-17,20-dimethylprosta-2,5,9,12,14-pentaenoic acid, (2E,5Z,9Z,14EZ)-11-oxo-15-(3-propylcyclopentyl)-16,17,18,19,20-pentanorprosta-2,5,9,12,14-pentaenoic acid, (2E,5Z,9Z,14EZ)-11-oxo-16-phenyl-17,18,19,20-tetranorprosta-2,5,9,12,14-pentaenoic acid, and (2E,5Z,9Z,14EZ)-11-oxo-16-(3-chlorophenoxy)-17,18,19,20-tetranorprosta-2,5,9,12,14-pentaenoic acid.

19. A pharmaceutical composition useful in the treatment of leukemia which comprises, as active ingredient, an effective amount of at least one trans-$\Delta^2$-prostaglandin derivative of the formula Ic depicted in claim 1, wherein the various symbols are as defined in claim 1, or a cyclodextrin clathrate thereof or, when R represents a hydrogen atom, a non-toxic salt thereof, in association with a pharmaceutical carrier or coating.

20. A method for the treatment of leukemia in a mammalian host which comprises administering to a host suffering from or subject to leukemia an effective amount of a prostaglandin derivative of formula Ic depicted in claim 1, wherein the various symbols are as defined in claim 1, or a cyclodextrin clathrate thereof, or, when R represents a hydrogen atom, a non-toxic salt thereof.

* * * * *